United States Patent
Sato et al.

(10) Patent No.: US 11,179,126 B2
(45) Date of Patent: *Nov. 23, 2021

(54) TOMOSYNTHESIS IMAGING APPARATUS AND METHOD FOR OPERATING THE SAME

(71) Applicant: FUJIFILM Corporation, Tokyo (JP)

(72) Inventors: Masaru Sato, Kanagawa (JP); Masayoshi Matsuura, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/565,515

(22) Filed: Sep. 10, 2019

(65) Prior Publication Data

US 2020/0100746 A1    Apr. 2, 2020

(30) Foreign Application Priority Data

Sep. 27, 2018  (JP) .............................. JP2018-182568

(51) Int. Cl.
*A61B 6/04* (2006.01)
*A61B 6/00* (2006.01)
(Continued)

(52) U.S. Cl.
CPC .............. *A61B 6/502* (2013.01); *A61B 6/025* (2013.01); *A61B 6/4007* (2013.01);
(Continued)

(58) Field of Classification Search
CPC ........... A61B 6/025; A61B 6/027; A61B 6/12; A61B 6/4007; A61B 6/4405;
(Continued)

(56) References Cited

U.S. PATENT DOCUMENTS 7,292,675 B1    11/2007  Li et al.
9,649,074 B2    5/2017   Simon et al.
(Continued)

FOREIGN PATENT DOCUMENTS

JP    2008023329    2/2008
JP    2011036399    2/2011
(Continued)

OTHER PUBLICATIONS

"Office Action of Japan Counterpart Application", dated May 11, 2021, with English translation thereof, pp. 1-6.

*Primary Examiner* — Irakli Kiknadze
(74) *Attorney, Agent, or Firm* — JCIPRNET

(57) ABSTRACT

A radiation source of a mammography apparatus includes plural first radiation tubes and one second radiation tube. The first radiation tubes are used for tomosynthesis imaging. In contrast, the second radiation tube is used for pre-imaging which is performed before the tomosynthesis imaging in order to set the irradiation conditions of radiation in the tomosynthesis imaging. The first radiation tubes are provided at plural positions where the focuses of the radiation are set so as to be arranged in a linear shape or an arc shape at equal intervals. The second radiation tube is provided at a position that is offset from the plural positions where the first radiation tubes are provided to a rear side which is a side opposite to the irradiation side of the radiation.

19 Claims, 18 Drawing Sheets

(51) Int. Cl.
*A61B 6/02* (2006.01)
*H01J 35/06* (2006.01)
*H01J 35/08* (2006.01)

(52) U.S. Cl.
CPC ............ *A61B 6/4411* (2013.01); *A61B 6/488* (2013.01); *A61B 6/54* (2013.01); *H01J 35/065* (2013.01); *H01J 35/112* (2019.05)

(58) Field of Classification Search
CPC ....... A61B 6/4452; A61B 6/481; A61B 6/487; A61B 6/488; A61B 6/504; A61B 6/5205; A61B 6/54; A61B 6/541; A61B 6/0414; A61B 6/107; A61B 6/4411; A61B 6/4441; A61B 6/502; A61B 6/542; A61B 6/032; A61B 6/06; A61B 6/4291; A61B 6/544; A61B 5/0059; A61B 6/04; A61B 6/4208; A61B 6/4233; A61B 6/4241; A61B 6/4417; A61B 6/461; A61B 6/469; A61B 6/545; A61B 6/56; A61B 6/482; A61B 6/5235; A61B 8/0825; A61B 6/5247; A61B 6/583; A61B 6/0435; A61B 6/5217; A61B 6/037; A61B 6/467; A61B 34/30; A61B 5/055; A61B 6/4429; A61B 6/5211; A61B 6/405; A61B 6/08; A61B 6/4283; A61B 6/505; A61B 6/5241; A61B 6/547; A61B 6/548; A61B 6/508; A61B 6/4035; A61B 10/04; A61B 6/42; A61B 6/4258; A61B 6/4085; A61B 6/4014; A61B 6/4071; A61B 6/4458; A61B 6/5264; A61B 6/14; A61B 6/145; A61B 6/463; A61B 6/466; H01J 35/06; H01J 35/10; H01J 35/065; H01J 35/112; G01N 23/046; G01N 23/044; G01N 2223/6126; G01N 2223/6123; G01N 23/04; G01N 2223/401; G01N 2223/419; G01N 2223/309; G01N 2223/408; G01N 2223/50; G01N 2223/612; G01N 23/083; G01N 21/359; G01N 21/6456; G01N 2223/03; G01N 2223/206; G01N 2223/301; G01N 2223/3302; G01N 2223/405; G01N 2223/601; G01N 23/20075; G01T 1/2018; A61M 5/007; G06T 2207/10116; G06T 2207/20224; G06T 2207/30101; G06T 5/50; G06T 7/0014; G06T 2207/10112; G06T 7/70; G06T 2200/04; G06T 2207/30004; G06T 2207/10081; G06T 11/005; G06T 11/008; G06T 19/00; G06T 2207/20116; G06T 2207/30168; G06T 2219/008; G06T 5/003; G06T 5/008; G06T 7/0002; G06T 7/12; G06T 7/136; H04N 5/32; A61N 5/1049; A61N 2005/1061; A61N 5/1067; A61N 5/1083; A61N 2005/1051; A61N 2005/1059; A61N 5/1065; A61N 5/1068; G16H 50/20; G16H 50/30
USPC .... 378/37, 62, 119, 124, 135, 137, 138, 145
See application file for complete search history.

(56) References Cited

U.S. PATENT DOCUMENTS

| | | |
|---|---|---|
| 10,660,580 B2 | 5/2020 | Heath et al. |
| 2007/0036265 A1* | 2/2007 | Jing ................... A61B 6/4028 378/37 |
| 2013/0208852 A1* | 8/2013 | Koishi .................. A61B 6/548 378/19 |
| 2015/0004312 A1 | 1/2015 | Scheer et al. |
| 2016/0007943 A1* | 1/2016 | Hoernig ................ A61B 6/482 378/37 |
| 2016/0256128 A1* | 9/2016 | Wang ...................... A61B 6/54 |

FOREIGN PATENT DOCUMENTS

| | | |
|---|---|---|
| JP | 2012050476 | 3/2012 |
| JP | 2013230404 | 11/2013 |
| JP | 2014166264 | 9/2014 |
| JP | 2016501080 | 1/2016 |
| JP | 2016503721 | 2/2016 |
| JP | 2016-135319 | 7/2016 |
| JP | 2017164426 | 9/2017 |
| WO | 2010-028208 | 3/2010 |

* cited by examiner

TOMOSYNTHESIS IMAGING APPARATUS AND METHOD FOR OPERATING THE SAME

CROSS-REFERENCE TO RELATED APPLICATION

This application claims priority from Japanese Patent Application No. 2018-182568, filed Sep. 27, 2018, the disclosure of which is incorporated herein by reference in its entirety.

BACKGROUND

Technical Field

The technology according to the present disclosure relates to a tomosynthesis imaging apparatus and a method for operating the same.

Related Art

A tomosynthesis imaging apparatus has been known which performs tomosynthesis imaging that moves a radiation source to a plurality of positions with respect to a radiation detector and emits radiation from the radiation source at each position (for example, see JP2016-135319A). The focuses of the radiation at the plurality of positions to which the radiation source is moved are set so as to be arranged, for example, in an arc shape at equal intervals. In the tomosynthesis imaging, the radiation is emitted to an imaging surface of the radiation detector at a plurality of irradiation angles and a plurality of projection images of an object irradiated with the radiation at different irradiation angles are captured. Then, tomographic images in any tomographic planes of the object are generated on the basis of the plurality of projection images.

The tomosynthesis imaging apparatus disclosed in JP2016-135319A is a mammography apparatus that uses the breast as the object. The radiation source includes one radiation tube having one focus and the radiation source including the one radiation tube is moved to each position. Paragraphs [0021] and [0022] disclose a configuration in which pre-imaging is performed with a lower dose and for a shorter irradiation time than tomosynthesis imaging before the tomosynthesis imaging and the irradiation conditions of radiation in the tomosynthesis imaging are set on the basis of an image obtained by the pre-imaging.

In the tomosynthesis imaging apparatus according to the related art, such as the tomosynthesis imaging apparatus disclosed in JP2016-135319A, the radiation source including one radiation tube is moved to each position. Therefore, there is a problem that the imaging time is relatively long and a burden on the subject increases.

For this reason, the inventors have examined a tomosynthesis imaging apparatus comprising a radiation source that includes a plurality of radiation tubes. However, in a case in which the radiation source includes a plurality of radiation tubes, the following problems related to pre-imaging have been found. The problems have not occurred in the radiation source according to the related art which includes one radiation tube.

That is, in a case in which one of the plurality of radiation tubes is used for both pre-imaging and tomosynthesis imaging, load is concentrated on the one radiation tube used for both pre-imaging and tomosynthesis imaging and the deterioration of the performance of the one radiation tube is faster than that of other radiation tubes.

An object of the technology according to the present disclosure is to provide a tomosynthesis imaging apparatus that can prevent the concentration of load on one radiation tube in a case in which a radiation source includes a plurality of radiation tubes and pre-imaging for setting the irradiation conditions of radiation in tomosynthesis imaging is performed and a method for operating the tomosynthesis imaging apparatus.

SUMMARY

In order to achieve the object, a tomosynthesis imaging apparatus according to the present disclosure comprises: a radiation detector that detects radiation transmitted through an object and has an imaging surface capturing a projection image of the object; a radiation source including a plurality of first radiation tubes that are provided at a plurality of positions where the radiation is emitted to the imaging surface at different irradiation angles and a second radiation tube different from the first radiation tubes; and a control unit that controls an operation of the radiation detector and the radiation source, performs pre-imaging for setting irradiation conditions of the radiation in tomosynthesis imaging, which captures a plurality of projection images of the object at different irradiation angles, using the second radiation tube before the tomosynthesis imaging, and performs the tomosynthesis imaging using the plurality of first radiation tubes.

Preferably, focuses of the radiation at the plurality of positions are set so as to be arranged in a linear shape or an arc shape at equal intervals.

Preferably, at least one of the plurality of first radiation tubes has one focus. Alternatively, it is preferable that at least one of the plurality of first radiation tubes has a plurality of the focuses.

Preferably, the second radiation tube is disposed at a position that is offset from the plurality of positions to a rear side which is a side opposite to an irradiation side of the radiation.

Preferably, a diameter of the second radiation tube is less than a diameter of each of the plurality of first radiation tubes.

Preferably, the second radiation tube is disposed at a position within a maximum scanning angle of the tomosynthesis imaging which is defined by positions at both ends among the plurality of positions. In this case, preferably, the second radiation tube is disposed at a position corresponding to a center of the maximum scanning angle within the maximum scanning angle.

Preferably, the second radiation tube is disposed at a position outside a maximum scanning angle of the tomosynthesis imaging which is defined by positions at both ends among the plurality of positions. In this case, preferably, the second radiation tube is disposed at a position that is outside the maximum scanning angle and is at a distance equal to or less than the interval from one of the positions at both ends.

Preferably, the radiation source includes a first housing that accommodates the first radiation tubes and a second housing that accommodates the second radiation tube, and the second housing is replaceable.

Preferably, the tomosynthesis imaging apparatus further comprises a radiation source accommodation portion that accommodates the radiation source and is provided with an accommodation space which accommodates the second housing such that the second housing is replaceable and an openable and closable cover which covers the accommodation space.

Preferably, each of the first radiation tube and the second radiation tube includes a cathode that emits electrons and an anode with which the electrons collide and which emits the radiation. Preferably, the anode is a fixed anode. In addition, preferably, the cathode is a field emission type including an electron emission source that emits an electron beam using a field emission phenomenon.

Preferably, the tomosynthesis imaging apparatus is a mammography apparatus that uses a breast as the object.

According to the present disclosure, there is provided a method for operating a tomosynthesis imaging apparatus comprising a radiation detector that detects radiation transmitted through an object and has an imaging surface capturing a projection image of the object and a radiation source including a plurality of first radiation tubes which are provided at a plurality of positions where the radiation is emitted to the imaging surface at different irradiation angles and a second radiation tube different from the first radiation tubes. The method comprises: a pre-imaging control step of performing pre-imaging for setting irradiation conditions of the radiation in tomosynthesis imaging, which captures a plurality of projection images of the object at different irradiation angles, using the second radiation tube before the tomosynthesis imaging; and a tomosynthesis imaging control step of performing the tomosynthesis imaging using the plurality of first radiation tubes.

According to the technology of the present disclosure, it is possible to provide a tomosynthesis imaging apparatus that can prevent the concentration of load on one radiation tube in a case in which a radiation source includes a plurality of radiation tubes and pre-imaging for setting the irradiation conditions of radiation in tomosynthesis imaging is performed and a method for operating the tomosynthesis imaging apparatus.

BRIEF DESCRIPTION OF THE DRAWINGS

Exemplary embodiments according to the technique of the present disclosure will be described in detail based on the following figures, wherein.

DETAILED DESCRIPTION

First Embodiment

Figure 1:
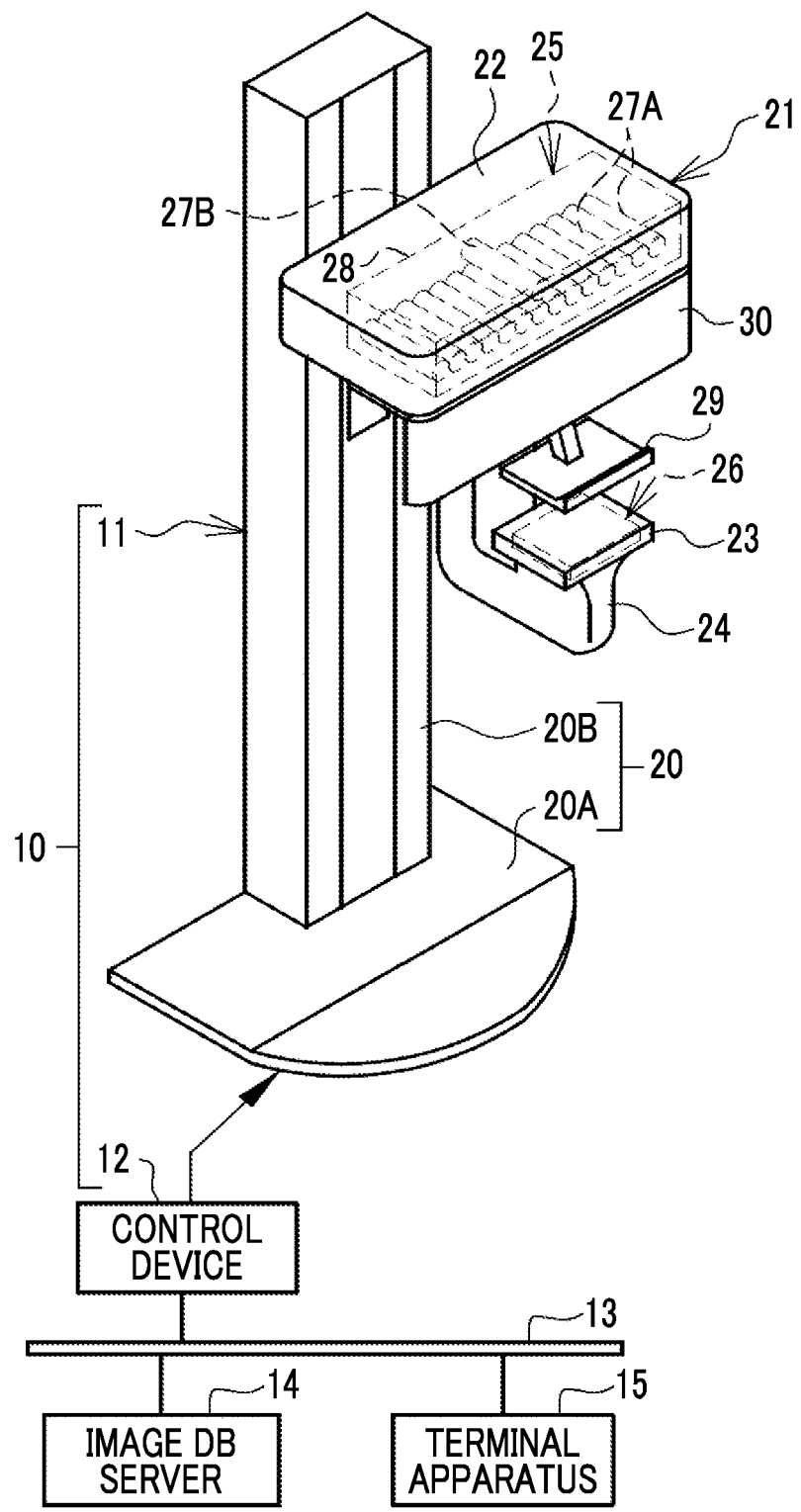
FIG. 1 is a diagram illustrating, for example, a mammography apparatus.
Figure 2:
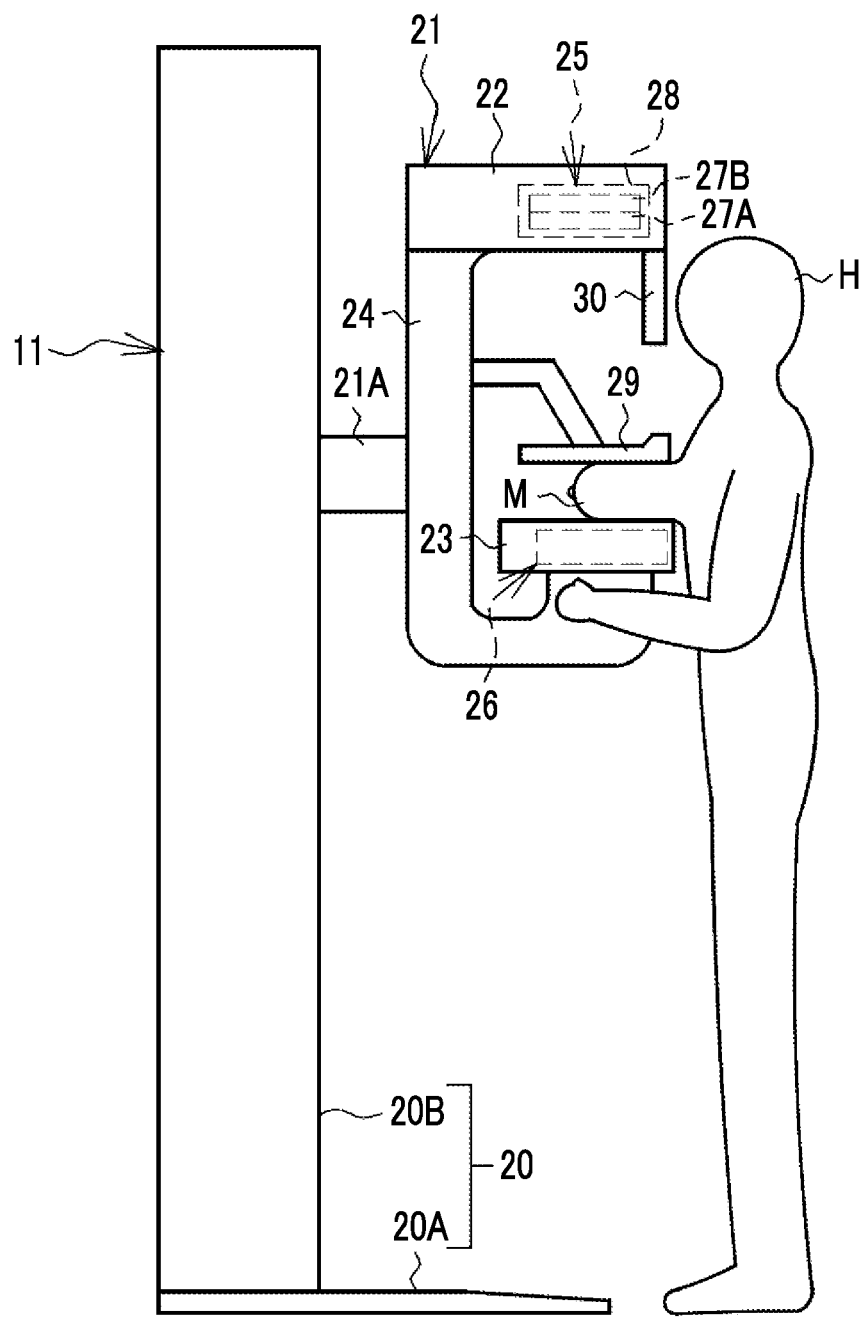
FIG. 2 is a diagram illustrating an apparatus main body of the mammography apparatus.

In FIGS. 1 and 2, a mammography apparatus 10 which is an example of a tomosynthesis imaging apparatus uses a breast M of a subject H as an object. The mammography apparatus 10 irradiates the breast M with radiation 37 (see, for example, FIG. 3), such as X-rays or γ-rays, to capture a radiographic image of the breast M.

The mammography apparatus 10 includes an apparatus main body 11 and a control device 12. The apparatus main body 11 is installed, for example, in a radiography room of a medical facility. The control device 12 is installed, for example, in a control room next to the radiography room. The control device 12 is connected to an image database (hereinafter, referred to as DB) server 14 through a network 13, such as a local area network (LAN), such that it can communicate with the image DB server. The image DB server 14 is, for example, a picture archiving and communication system (PACS) server, receives a radiographic image from the mammography apparatus 10, and accumulates and manages the radiographic image.

A terminal apparatus 15 is also connected to the network 13. The terminal apparatus 15 is, for example, a personal computer that is used by a doctor to make a diagnosis based on the radiographic image. The terminal apparatus 15 receives the radiographic image from the image DB server 14 and displays the radiographic image on a display.

The apparatus main body 11 includes a stand 20 and an arm 21. The stand 20 includes a pedestal 20A that is provided on the floor of the radiography room and a support 20B that extends from the pedestal 20A in a height direction. The arm 21 has a substantially C-shape in a side view and is connected to the support 20B through a connection portion 21A. The arm 21 can be moved with respect to the support 20B in the height direction by the connection portion 21A and the height of the arm 21 can be adjusted according to the height of the subject H by the connection portion 21A. In addition, the arm 21 is rotatable on a rotation axis perpendicular to the support 20B through the connection portion 21A.

The arm 21 includes a radiation source accommodation portion 22, a detector accommodation portion 23, and a main body portion 24. The radiation source accommodation portion 22 accommodates a radiation source 25. The detector accommodation portion 23 accommodates a radiation detector 26. In addition, the detector accommodation portion 23 functions as an imaging table on which the breast M is placed. The main body portion 24 integrally connects the radiation source accommodation portion 22 and the detector accommodation portion 23. The radiation source accommodation portion 22 is provided on the upper side in the height direction and the detector accommodation portion 23 is provided on the lower side in the height direction at a posture where the detector accommodation portion 23 faces the radiation source accommodation portion 22.

The radiation source 25 includes a plurality of first radiation tubes 27A, for example, 14 first radiation tubes 27A, one second radiation tube 27B, and a housing 28 that accommodates the radiation tubes 27A and 27B. The first radiation tubes 27A are used for tomosynthesis imaging which captures a plurality of projection images of the breast M at different irradiation angles as radiographic images. The second radiation tube 27B is used for pre-imaging which is performed before the tomosynthesis imaging in order to set the irradiation conditions of the radiation 37 in the tomosynthesis imaging. The radiation detector 26 detects the radiation 37 transmitted through the breast M and outputs a radiographic image.

A compression plate 29 is attached between the radiation source accommodation portion 22 and the detector accommodation portion 23 in the main body portion 24. The compression plate 29 is made of a material that transmits the radiation 37. The compression plate 29 is provided so as to face the detector accommodation portion 23. The compression plate 29 can be moved in a direction toward the detector accommodation portion 23 and a direction away from the detector accommodation portion 23. The compression plate 29 is moved toward the detector accommodation portion 23 and compresses the breast M interposed between the detector accommodation portion 23 and the compression plate 29.

A face guard 30 is attached to a lower part of the front surface of the radiation source accommodation portion 22. The face guard 30 protects the face of the subject H from the radiation 37.

A tube voltage generator (not illustrated) that generates a tube voltage applied to each of the radiation tubes 27A and 27B is provided in the support 20B. In addition, a voltage cable (not illustrated) extending from the tube voltage generator is provided in the support 20B. The voltage cable further extends from the connection portion 21A into the radiation source accommodation portion 22 through the arm 21 and is connected to the radiation source 25.

Figure 3:
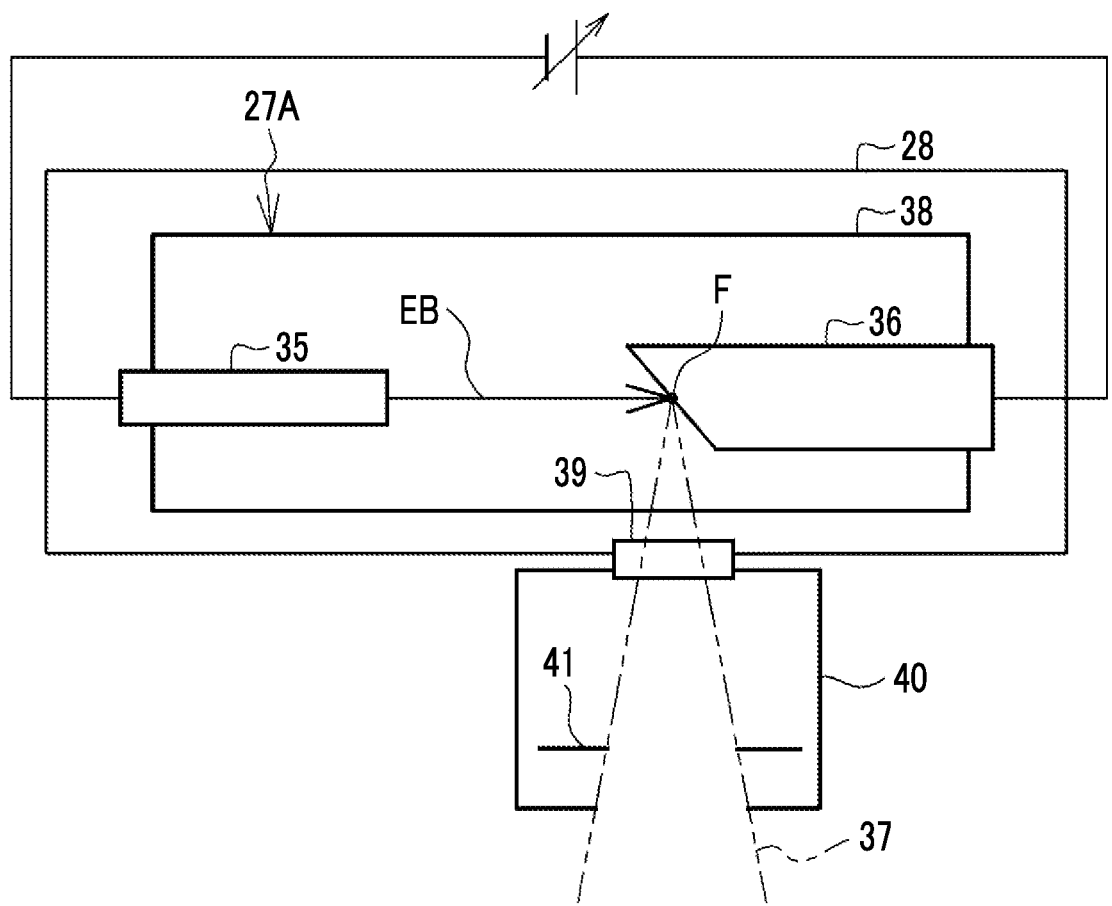
FIG. 3 is a diagram illustrating a first radiation tube.

In FIG. 3, the first radiation tube 27A includes a cathode 35 and an anode 36. The cathode 35 emits electrons. The electrons collide with the anode 36 and the anode 36 emits the radiation 37. The cathode 35 and the anode 36 are accommodated in a vacuum glass tube 38. The cathode 35 is an electron emission type including an electron emission source that emits an electron beam EB to the anode 36, using a field emission phenomenon. The anode 36 is a fixed anode which is not rotated and whose position is fixed, unlike a rotating anode that is rotated by a rotation mechanism.

The tube voltage generator applies a tube voltage between the cathode 35 and the anode 36. The electron beam EB is emitted from the cathode 35 to the anode 36 by the application of the tube voltage. Then, the radiation 37 is emitted from a point (hereinafter, referred to as a focus) F of the anode 36 where the electron beam EB collides.

The housing 28 is provided with a radiation transmission window 39 that transmits the radiation 37. The radiation 37 emitted from the anode 36 is emitted to the outside of the housing 28 through the radiation transmission window 39. In addition, the housing 28 is filled with insulating oil. Since the second radiation tube 27B has the same configuration as the first radiation tube 27A, the illustration and description thereof will be omitted.

An irradiation field limiter 40 (not illustrated in FIGS. 1 and 2) is provided below the radiation transmission window 39 in the height direction. The irradiation field limiter 40 is also called a collimator and sets the irradiation field of the radiation 37 in an imaging surface 45 (see FIG. 4) of the radiation detector 26. Specifically, the irradiation field limiter 40 includes a plurality of shielding plates 41 which are made of, for example, lead and shield the radiation 37 transmitted through the radiation transmission window 39. The shielding plates 41 are moved to change the size of, for example, a rectangular irradiation opening defined by the shielding plates 41, thereby setting the irradiation field of the radiation 37.

The irradiation field limiter 40 is provided in each of the radiation tubes 27A and 27B. Therefore, the irradiation fields of the radiation 37 emitted from the radiation tubes 27A and 27B can be individually set. In addition, the number of irradiation field limiters 40 provided in each of the radiation tubes 27A and 27B may be less than the above-mentioned value. For example, only one irradiation field limiter 40 may be provided and the one irradiation field limiter 40 may be moved between the radiation tubes 27A and 27B.

Figure 4:
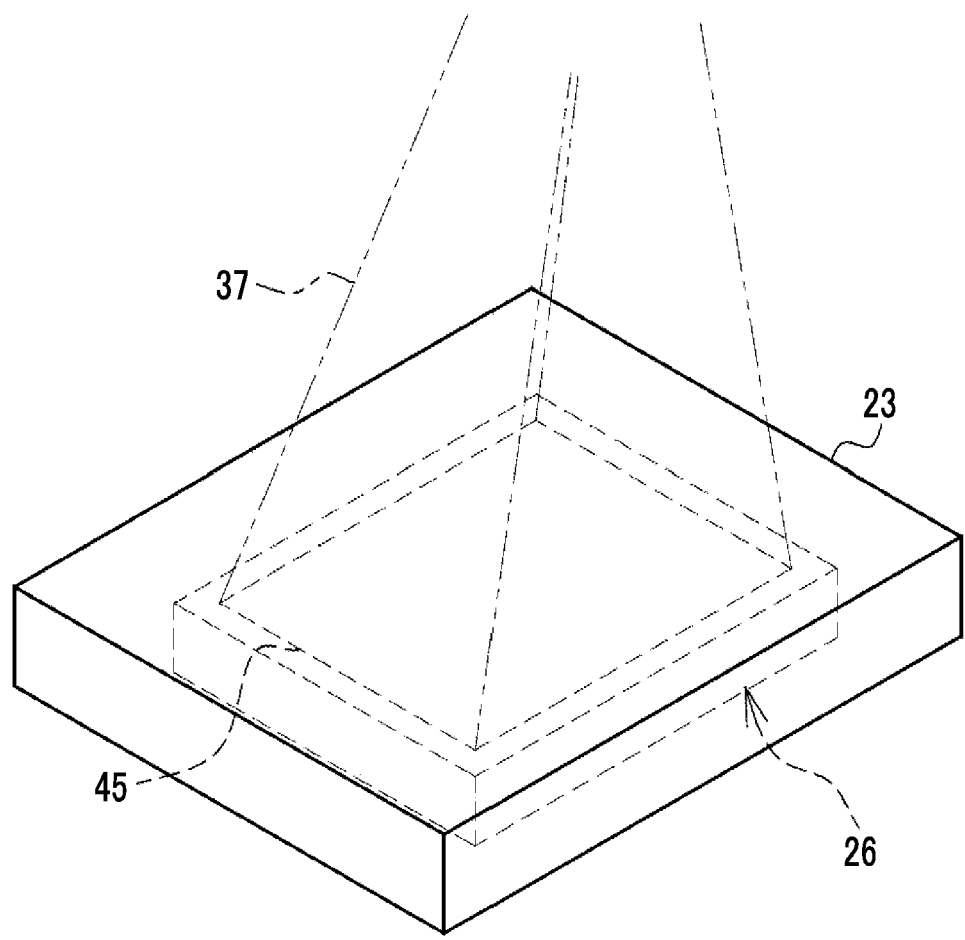
FIG. 4 is a diagram illustrating a detector accommodation portion.

In FIG. 4 illustrating the detector accommodation portion 23, the radiation detector 26 has the imaging surface 45. The imaging surface 45 detects the radiation 37 transmitted through the breast M and captures a projection image of the breast M. Specifically, the imaging surface 45 is a two-dimensional plane in which pixels converting the radiation 37 into an electric signal are two-dimensionally arranged. The radiation detector 26 is also referred to as a flat panel detector (FPD). The radiation detector 26 may be an indirect conversion type that includes, for example, a scintillator converting the radiation 37 into visible light and converts visible light emitted from the scintillator into an electric signal or a direct conversion type that directly converts the radiation 37 into an electric signal.

Figure 5:
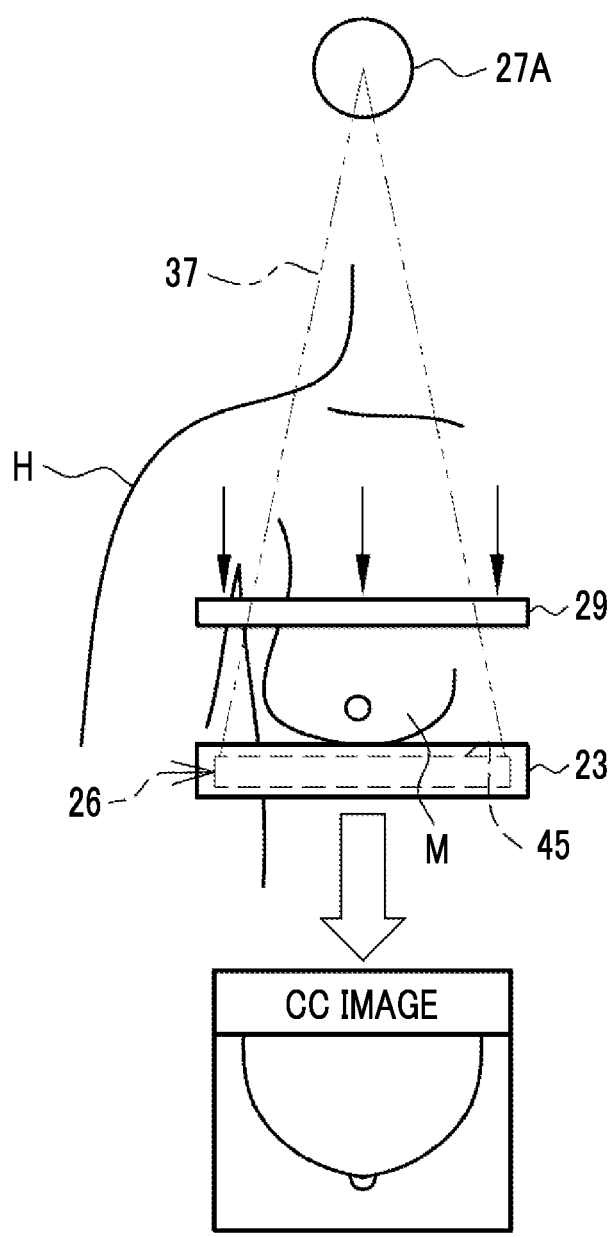
FIG. 5 is a diagram illustrating an aspect of CC imaging.
Figure 6:
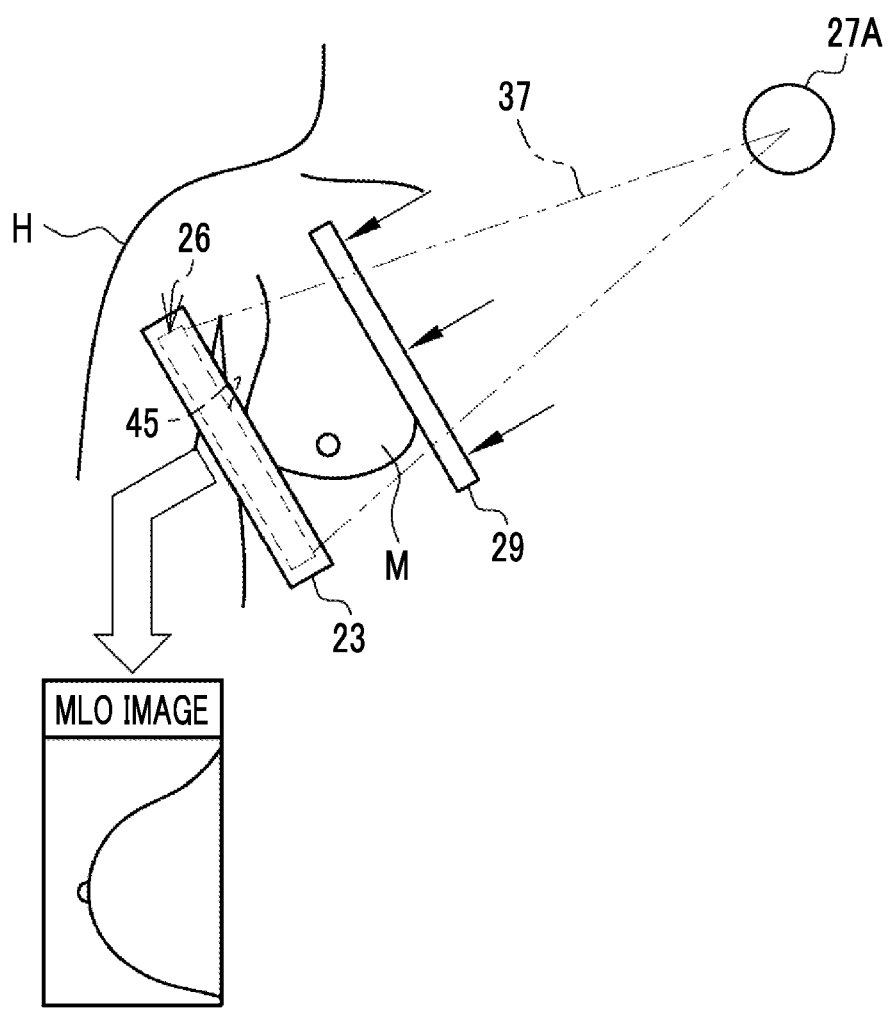
FIG. 6 is a diagram illustrating an aspect of MLO imaging.

FIGS. 5 and 6 illustrate a method for capturing an image of the breast M in the mammography apparatus 10. FIG. 5 illustrates craniocaudal view (CC) imaging and FIG. 6 illustrates mediolateral oblique view (MLO) imaging. The CC imaging is an imaging method which captures an image while compressing the breast M interposed between the detector accommodation portion 23 and the compression plate 29 in the vertical direction. In this case, the radiation detector 26 outputs a CC image as the projection image. In contrast, the MLO imaging is an imaging method which captures an image while compressing the breast M interposed between the detector accommodation portion 23 and the compression plate 29 at an inclination angle of about 60°. In this case, the radiation detector 26 outputs an MLO image as the projection image. In addition, FIGS. 5 and 6 illustrate only one first radiation tube 27A for simplicity of illustration. Further, FIGS. 5 and 6 illustrate the right breast M. Of course, the image of the left breast M can be captured.

Figure 7:
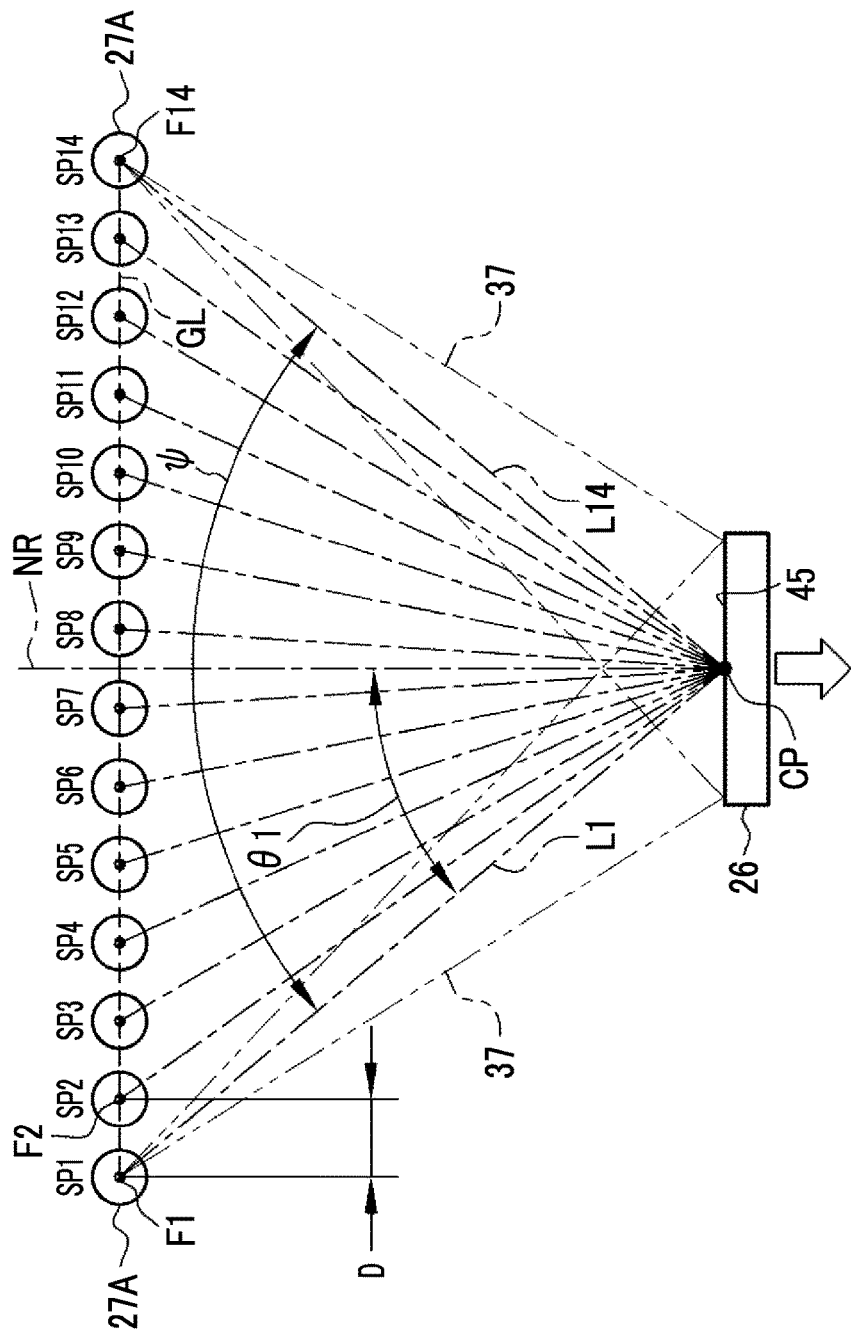
FIG. 7 is a diagram illustrating an aspect of tomosynthesis imaging.

In FIG. 7 which is a plan view illustrating the radiation source 25 and the radiation detector 26 as viewed from the support 20B, it is assumed that the direction of a normal line to the imaging surface 45 is the Z direction, a direction along a side of the imaging surface 45 is the X direction, and a depth direction of the imaging surface 45 which is perpendicular to the Z direction and the X direction is the Y direction. The first radiation tubes 27A are provided at a total of 14 positions SP1, SP2, . . . , SP13, and SP14 where the radiation 37 is emitted to the imaging surface 45 at different irradiation angles. For the positions SP1 to SP14, the focuses F1 to F14 of the radiation 37 in the first radiation tubes 27A at the positions SP1 to SP14 are set so as to be linearly arranged at equal intervals D. In addition, the positions SP1 to SP14 are bilaterally symmetric with respect to a normal line NR to the imaging surface 45 which extends from a center point CP of the side of the imaging surface 45 along the X direction such that the positions SP1 to SP7 are disposed on the left side of the normal line NR and the positions SP8 to SP14 are disposed on the right side of the normal line NR.

Here, a straight line GL on which the positions SP1 to SP14 are set is parallel to the side of the imaging surface 45 along the X direction in a plan view of the radiation source 25 and the radiation detector 26 from the Z direction. The straight line GL is offset to the front side (a side opposite to the support 20B) in the Y direction. The present disclosure is not limited to a case in which the intervals D between the focuses F1 to F14 are exactly equal to each other. For example, an error of ±5% is allowed.

The irradiation angle of the radiation 37 is an angle formed between the normal line NR and a line connecting the center point CP and each of the focuses F1 to F14 of the radiation 37 in the first radiation tubes 27A at the positions SP1 to SP14. For example, FIG. 7 illustrates a line L1 connecting the focus F1 at the position SP1 and the center point CP and an irradiation angle θ1 formed between the normal line NR and the line L1.

An angle represented by a symbol $\psi$ is the maximum scanning angle of tomosynthesis imaging. The maximum scanning angle $\psi$ is defined by the positions SP1 and SP14 at both ends among the positions SP1 to SP14. Specifically, the maximum scanning angle is an angle formed between the line L1 connecting the focus F1 at the position SP1 and the center point CP and a line L14 connecting the focus F14 at the position SP14 and the center point CP.

In one tomosynthesis imaging operation, the first radiation tubes 27A are driven one by one in the order of the first radiation tube 27A at the position SP1, the first radiation tube 27A at the position SP2, . . . , the first radiation tube 27A at the position SP13, and the first radiation tube 27A at the position SP14 to irradiate the breast M with the radiation 37. The radiation detector 26 detects the radiation 37 emitted at each of the positions SP1 to SP14 whenever the radiation 37 is emitted and outputs projection images at the positions SP1 to SP14. The tomosynthesis imaging can be performed by both the CC imaging method illustrated in FIG. 5 and the MLO imaging method illustrated in FIG. 6. In the case of simple imaging in which the CC imaging illustrated in FIG. 5 and the MLO imaging illustrated in FIG. 6 are independently performed, the first radiation tube 27A at the position SP7 or the position SP8 where the irradiation angle θ is approximately 0° is used.

Figure 8:
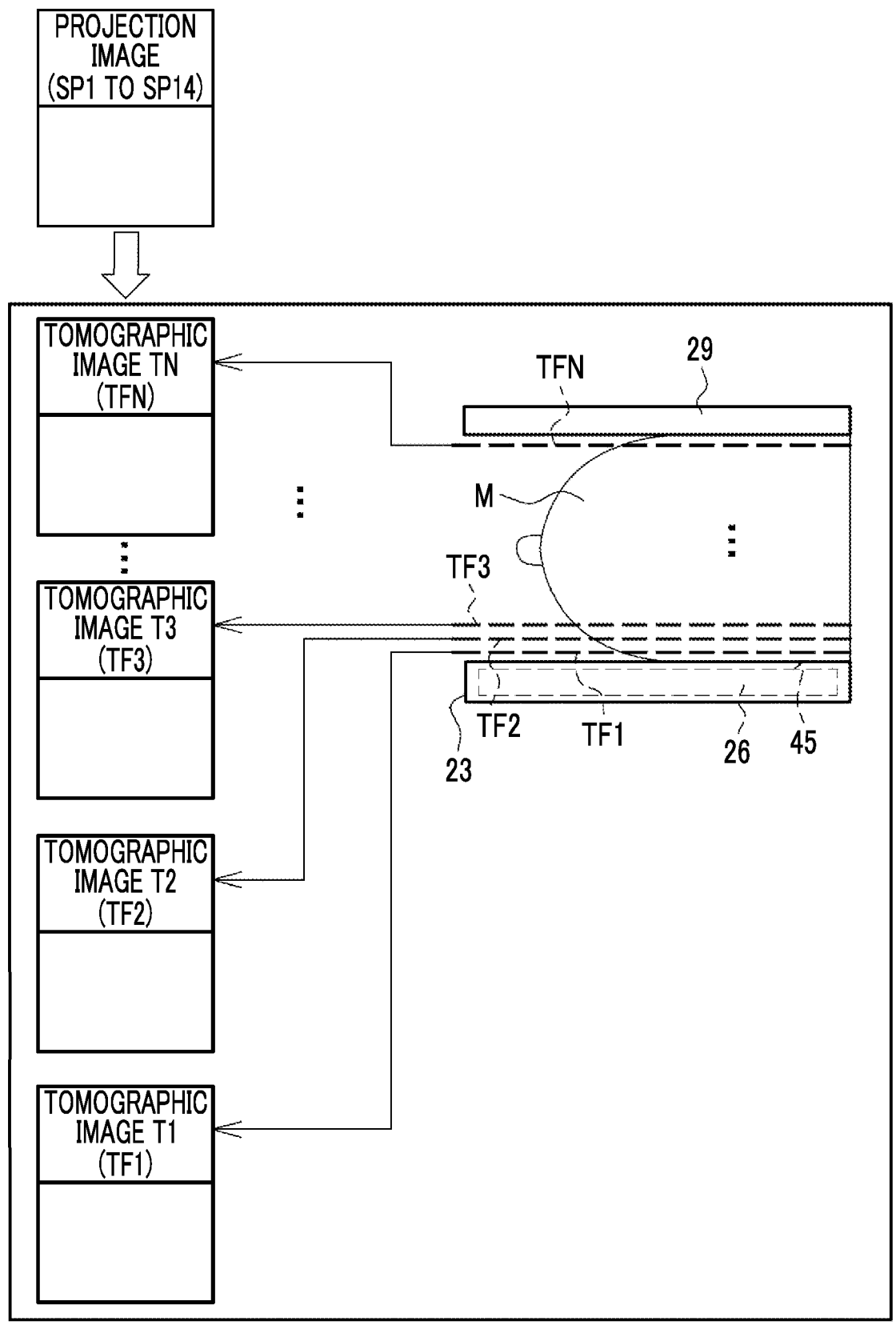
FIG. 8 is a diagram illustrating an aspect in which tomographic images are generated from a plurality of projection images obtained by the tomosynthesis imaging.

As illustrated in FIG. 8, the mammography apparatus 10 generates tomographic images T1 to TN corresponding to any tomographic planes TF1 to TFN of the breast M from the plurality of projection images at the plurality of positions SP1 to SP14 obtained by the tomosynthesis imaging illustrated in FIG. 7, using a known method such as a filtered back projection method. In the tomographic images T1 to TN, images in which structures in the tomographic planes TF1 to TFN have been highlighted are obtained.

Figure 9:
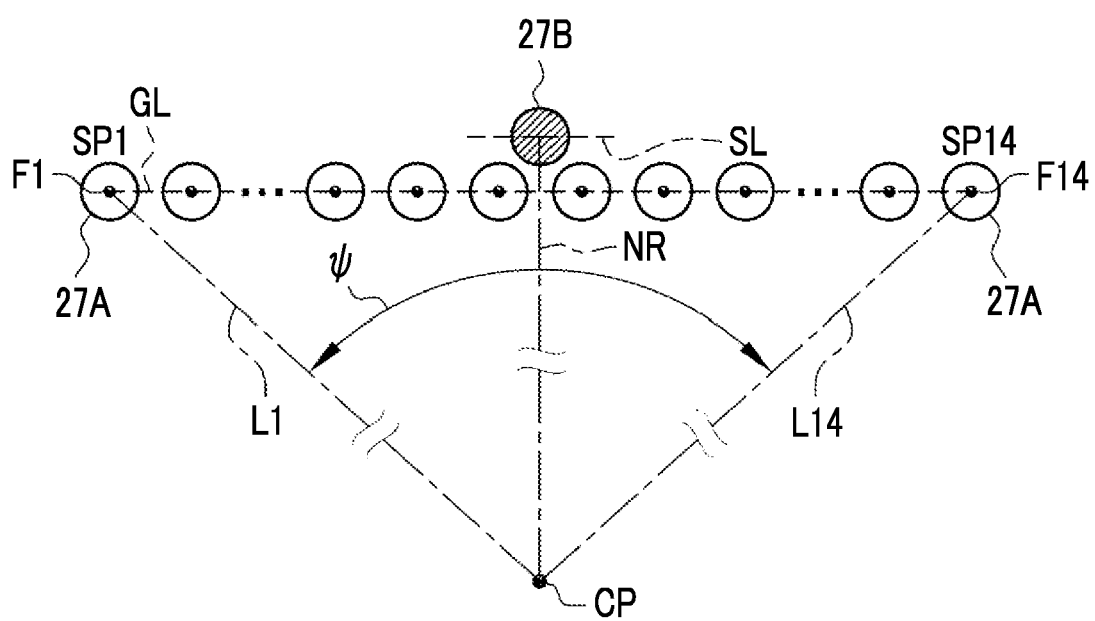
FIG. 9 is a diagram illustrating the arrangement position of a second radiation tube.

In FIG. 9, the second radiation tube 27B is disposed at a position corresponding to the center of the maximum scanning angle $\psi$ within the maximum scanning angle $\psi$. In this example, that is, the position corresponding to the center of the maximum scanning angle $\psi$ is a position on the normal line NR. In addition, the second radiation tube 27B is disposed at a position that is offset from the plurality of positions SP1 to SP14 to the rear side which is a side opposite to the irradiation side of the radiation 37, as represented by the straight line GL and an auxiliary line SL that is parallel to the straight line GL and passes through the second radiation tube 27B.

Figure 10:
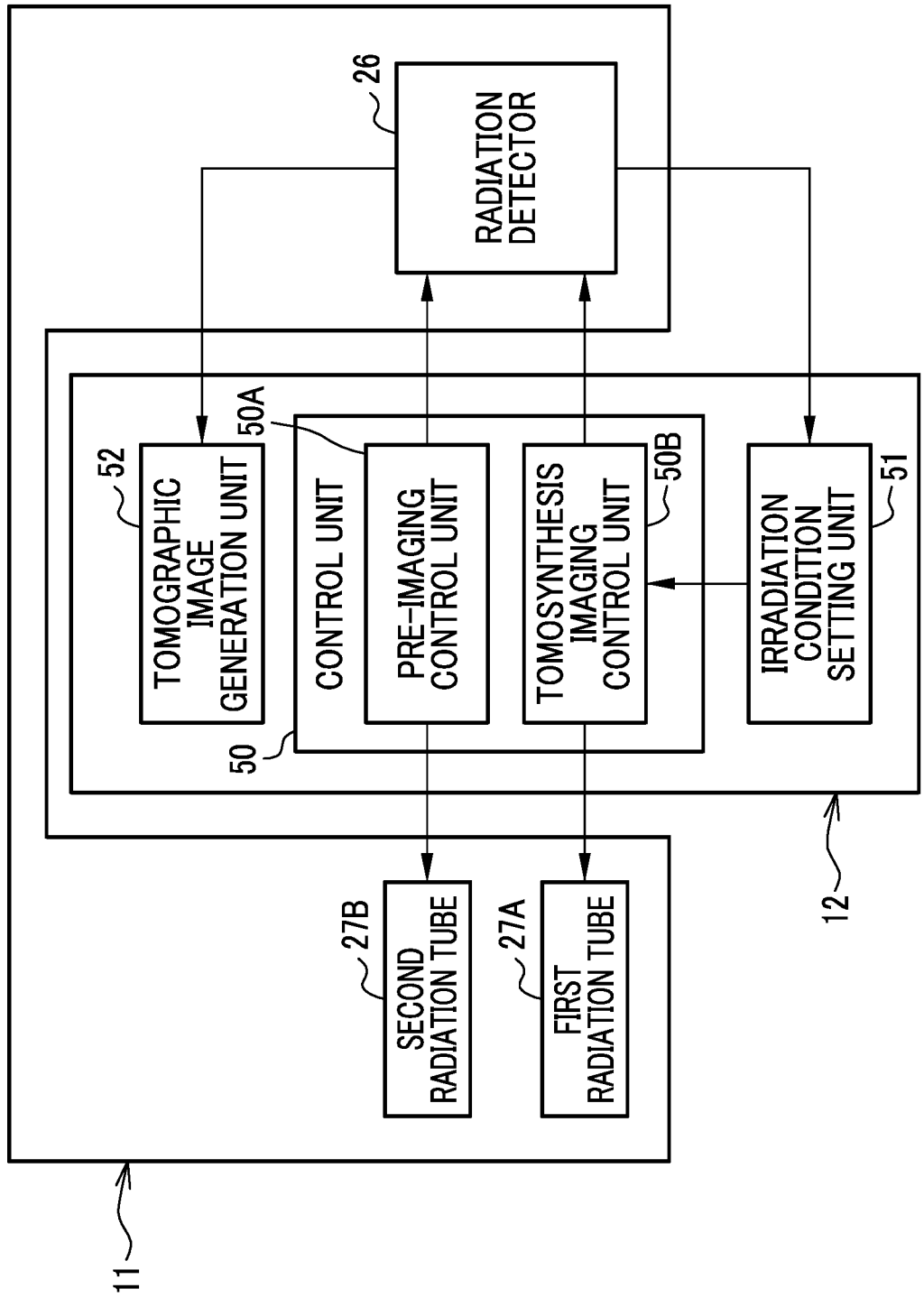
FIG. 10 is a block diagram illustrating a control device.

In FIG. 10, the control device 12 comprises a control unit 50, an irradiation condition setting unit 51, and a tomographic image generation unit 52.

The control unit 50 controls the operation of the radiation source 25 and the radiation detector 26. The control unit 50 is provided with a pre-imaging control unit 50A and a tomosynthesis imaging control unit 50B. The pre-imaging control unit 50A performs pre-imaging using the second radiation tube 27B. Specifically, the pre-imaging control unit 50A drives the second radiation tube 27B under predetermined pre-imaging irradiation conditions such that the radiation 37 is emitted from the second radiation tube 27B. Then, a projection image detected by the radiation detector 26 is output from the radiation detector 26 to the irradiation condition setting unit 51.

The irradiation condition setting unit 51 analyzes the projection image from the radiation detector 26 in the pre-imaging and sets the irradiation conditions of the radiation 37 in the tomosynthesis imaging. The irradiation condition setting unit 51 outputs the set irradiation conditions to the tomosynthesis imaging control unit 50B.

The irradiation conditions include a tube voltage applied to the first radiation tube 27A, a tube current, and the time for which the radiation 37 is emitted. An example of the setting of the irradiation conditions is increasing the tube voltage to a rated value in a case in which the thickness of the breast M is relatively large and the density of the projection image from the radiation detector 26 is lower than a desired level. In a case in which the irradiation conditions are set on the basis of the pre-imaging, the density of the projection image captured by the tomosynthesis imaging and the density of the tomographic image T generated from the projection image are at a substantially constant level regardless of an individual difference in the breast M. In addition, instead of the tube current and the irradiation time, a tube current-irradiation time product (a so-called mAs value) may be used as the irradiation conditions.

The tomosynthesis imaging control unit 50B performs the tomosynthesis imaging illustrated in FIG. 7 using the plurality of first radiation tubes 27A. Specifically, the tomosynthesis imaging control unit 50B drives the plurality of first radiation tubes 27A under the irradiation conditions set by the irradiation condition setting unit 51 such that the plurality of first radiation tubes 27A sequentially irradiate the breast M with the radiation 37. Then, a plurality of projection images detected by the radiation detector 26 are output from the radiation detector 26 to the tomographic image generation unit 52.

As illustrated in FIG. 8, the tomographic image generation unit 52 generates tomographic images T on the basis of the plurality of projection images from the radiation detector 26. The tomographic image generation unit 52 transmits the generated tomographic images T to the image DB server 14 through the network 13.

In FIG. 10, the irradiation field limiter 40 is not illustrated for simplicity of illustration. The pre-imaging control unit 50A and the tomosynthesis imaging control unit 50B also control the operation of the irradiation field limiter 40. Specifically, the pre-imaging control unit 50A and the tomosynthesis imaging control unit 50B move the shielding plate 41 of the irradiation field limiter 40 corresponding to a radiation tube that emits the radiation 37 among the radiation tubes 27A and 27B to set the irradiation field.

Figure 11:
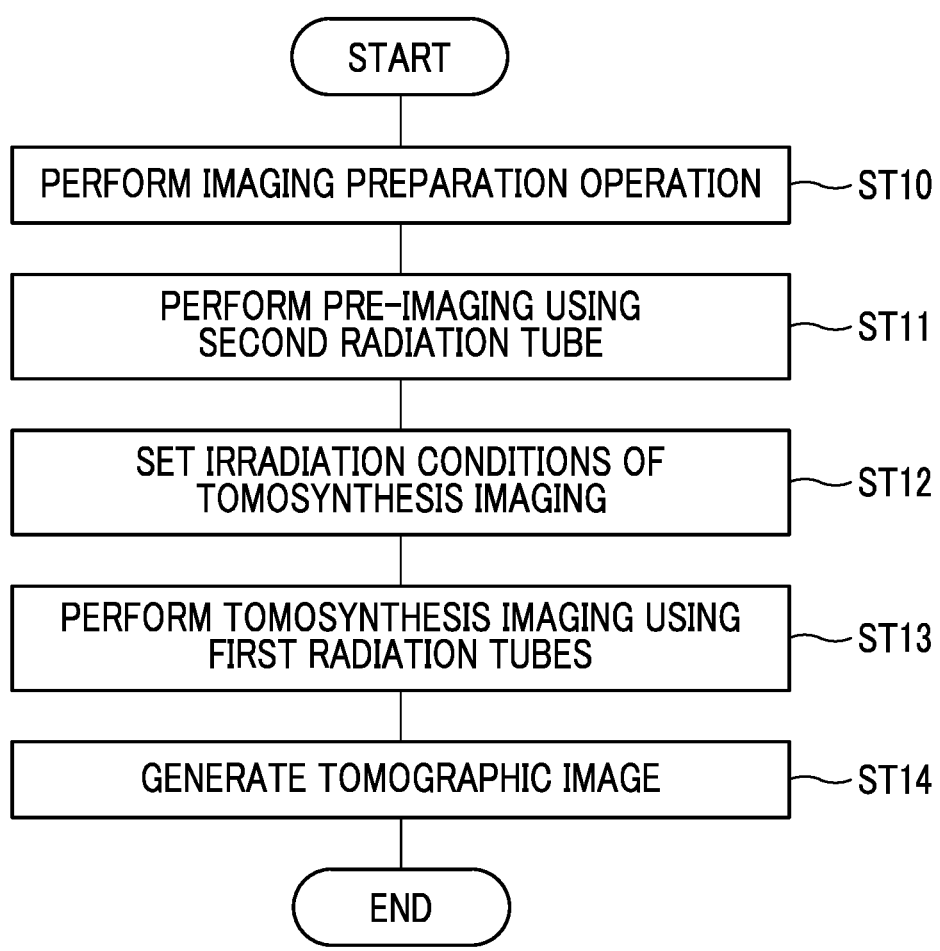
FIG. 11 is a flowchart illustrating the procedure of tomosynthesis imaging by the mammography apparatus.

Next, the operation of the above-mentioned configuration will be described with reference to a flowchart illustrated in FIG. 11. The procedure of the tomosynthesis imaging by the mammography apparatus 10 starts from an imaging preparation operation in Step ST10. The imaging preparation operation is performed by a radiology technician who operates the mammography apparatus 10 and is mainly related to the positioning of the breast M. For example, the imaging preparation operation includes an operation which guides the subject H to the apparatus main body 11 such that the breast M is placed on the detector accommodation portion 23, moves the compression plate 29 to the detector accommodation portion 23, and compresses the breast M interposed between the compression plate 29 and the detector accommodation portion 23. After the imaging preparation operation ends, the radiology technician inputs a command to start tomosynthesis imaging.

Before the tomosynthesis imaging, as illustrated in Step ST11, the pre-imaging control unit 50A performs the pre-imaging using the second radiation tube 27B (pre-imaging control step).

The second radiation tube 27B that is different from the first radiation tube 27A for tomosynthesis imaging is used for the pre-imaging. Therefore, a situation does not occur in which load is concentrated on one radiation tube used for both the pre-imaging and the tomosynthesis imaging and the deterioration of the performance of the radiation tube is faster than that of other radiation tubes as in a case in which one of the plurality of radiation tubes is used for both the pre-imaging and the tomosynthesis imaging.

In a case in which some (for example, all) of the plurality of radiation tubes are used for both the pre-imaging and the tomosynthesis imaging, it is necessary to correct the projection image obtained by the pre-imaging, using different correction methods for each radiation tube, in order to absorb the individual difference between some of the radiation tubes that are used for both the pre-imaging and the tomosynthesis imaging. As a result, the process becomes complicated. However, in this embodiment, since the pre-imaging is performed by the dedicated second radiation tube 27B, it is possible to prevent a correction process for the projection image obtained by the pre-imaging from being complicated.

In a case in which the second radiation tube 27B is disposed at a position between two adjacent first radiation tubes 27A, the presence of the second radiation tube 27B is likely to disturb the regularity of the intervals D between the focuses F1 to F14. In a case in which the regularity of the intervals D between the focuses F1 to F14 is disturbed, the process related to the generation of the tomographic image T is complicated. However, in this embodiment, as illustrated in FIG. 9, the second radiation tube 27B is disposed at a position that is offset from the plurality of positions SP1 to SP14 to the rear side which is a side opposite to the irradiation side of the radiation 37. Therefore, the possibility that the regularity of the intervals D between the focuses F1 to F14 will be disturbed by the presence of the second radiation tube 27B is reduced and the concern that the process related to the generation of the tomographic image T will be complicated is reduced.

As also illustrated in FIG. 9, the second radiation tube 27B is disposed at a position corresponding to the center of the maximum scanning angle of the tomosynthesis imaging which is defined by the positions SP1 and SP14 at both ends among the plurality of positions SP1 to SP14 within the maximum scanning angle $\psi$. Therefore, the projection image output from the radiation detector 26 in the pre-imaging has been obtained by emitting the radiation 37 at the same position as that in the tomosynthesis imaging. In addition, the projection image output from the radiation detector 26 in the pre-imaging includes the image information of the breast M required to set the irradiation conditions of the radiation 37 without any bias in the left-right direction with reference to the center of the maximum scanning angle $\psi$.

The projection image output from the radiation detector 26 in the pre-imaging is output to the irradiation condition setting unit 51. The irradiation condition setting unit 51 sets the irradiation conditions of the radiation 37 in the tomosynthesis imaging on the basis of the projection image from the radiation detector 26 (Step ST12). The set irradiation conditions are output from the irradiation condition setting unit 51 to the tomosynthesis imaging control unit 50B.

Then, as illustrated in Step ST13, the tomosynthesis imaging control unit 50B performs the tomosynthesis imaging illustrated in FIG. 7 using the first radiation tubes 27A (tomosynthesis imaging control step).

In the first radiation tubes 27A, the focuses F1 to F14 of the radiation 37 are disposed at the plurality of positions SP1 to SP14 which are set so as to be linearly arranged at equal intervals D. Since the regularity of the arrangement positions SP1 to SP14 of the first radiation tubes 27A is ensured, it is possible to simplify the process related to the generation of the tomographic image T.

As illustrated in FIG. 3, the first radiation tube 27A includes the field-emission-type cathode 35 and the anode 36 which is a fixed anode. The field-emission-type cathode 35 generates a much smaller amount of heat than a cathode with a filament structure which emits thermal electrons. Therefore, a heat dissipation structure is unnecessary and it is possible to reduce the size of the radiation tube. In addition, the fixed anode does not require a rotating mechanism unlike a rotating anode and it is also possible to reduce the size of the radiation tube. Therefore, a larger number of first radiation tubes 27A can be disposed in a limited space of the housing 28. In a case in which a larger number of first radiation tubes 27A can be disposed, it is possible to obtain a larger number of projection images in the tomosynthesis imaging. Therefore, the amount of image information used to generate the tomographic image T increases, which makes it possible to improve the quality of the tomographic image T.

Similarly to the first radiation tube 27A, the second radiation tube 27B includes the field-emission-type cathode 35 and the anode 36 which is a fixed anode. Therefore, it is possible to minimize an increase in the size of the radiation source 25 due to the provision of the second radiation tube 27B only for pre-imaging.

The projection image output from the radiation detector 26 in the tomosynthesis imaging is output to the tomographic image generation unit 52. As illustrated in FIG. 8, the tomographic image generation unit 52 generates the tomographic image T on the basis of the projection image from the radiation detector 26 (Step ST14). The generated tomographic image T is transmitted from the tomographic image generation unit 52 to the image DB server 14.

In addition, the second radiation tube 27B may not be disposed at the position that is offset to the rear side, but may be disposed at a position between two adjacent first radiation tubes 27A.

Second Embodiment

Figure 12:
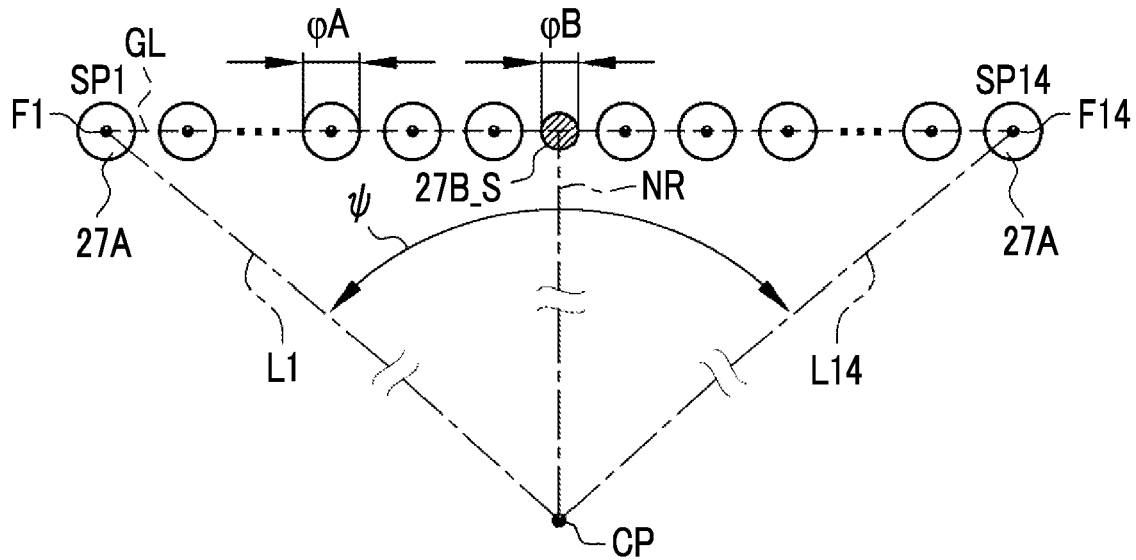
FIG. 12 is a diagram illustrating a second radiation tube having a smaller diameter than a first radiation tube.

In a second embodiment illustrated in FIG. 12, a second radiation tube 27B_S having a smaller diameter than each of a plurality of first radiation tubes 27A is used.

In FIG. 12, the second radiation tube 27B_S is disposed at a position corresponding to the center of the maximum scanning angle between two adjacent first radiation tubes 27A. The second radiation tube 27B has a diameter φB less than the diameter φA of each of the plurality of first radiation tubes 27A (φB<φA). For example, φB is half of φA.

As such, in the second embodiment, the diameter φB of the second radiation tube 27B_S is less than the diameter φA of each of the plurality of first radiation tubes 27A. Therefore, the possibility that the regularity of the intervals D between the focuses F1 to F14 will be disturbed is reduced and the concern that the process related to the generation of the tomographic image T will be complicated is reduced, as compared to a case in which the first radiation tubes 27A and the second radiation tube 27B have the same diameter.

In a case in which the diameter φB is reduced, the maximum dose of the radiation 37 is reduced. However, since the pre-imaging does not require a very high dose, there is no particular problem even in a case in which the diameter φB is reduced.

Figure 13:
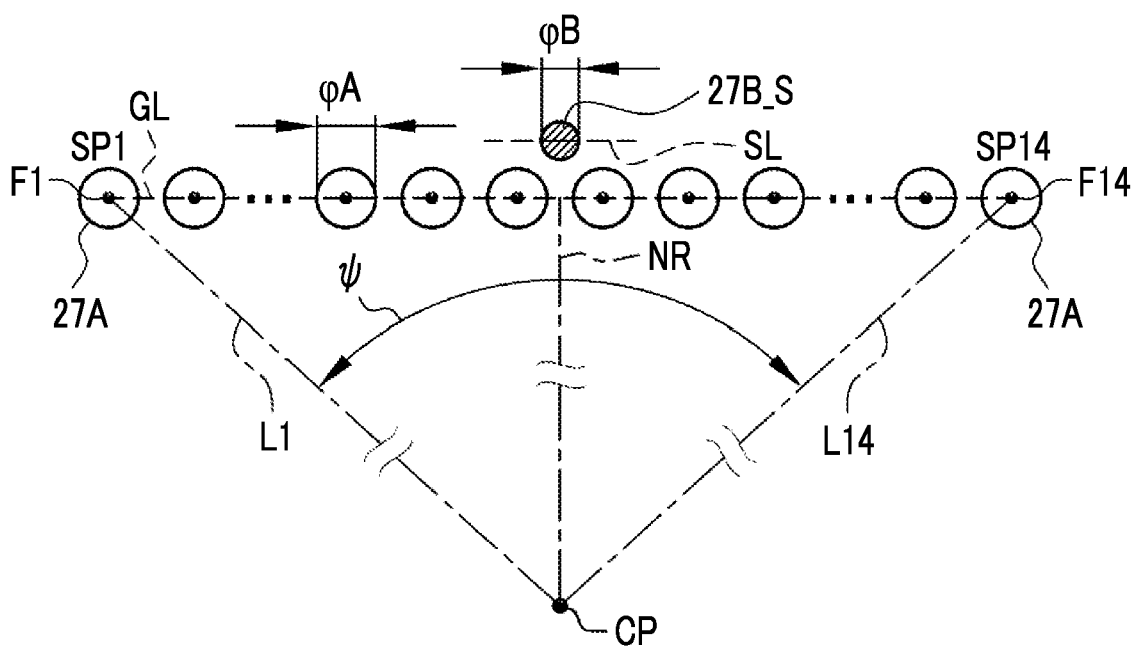
FIG. 13 is a diagram illustrating a second radiation tube that is disposed at a position offset to the rear side and has a smaller diameter than the first radiation tube.

In addition, as illustrated in FIG. 13, the first embodiment in which the second radiation tube 27B is disposed at the position that is offset to the rear side and the second embodiment in which the second radiation tube 27B_S having the diameter φB less than the diameter φA of the first radiation tube 27A is disposed may be combined with each other. In this case, the possibility that the regularity of the intervals D between the focuses F1 to F14 will be disturbed is further reduced and the concern that the process related to the generation of the tomographic image T will be complicated is further reduced.

Third Embodiment

Figure 14:
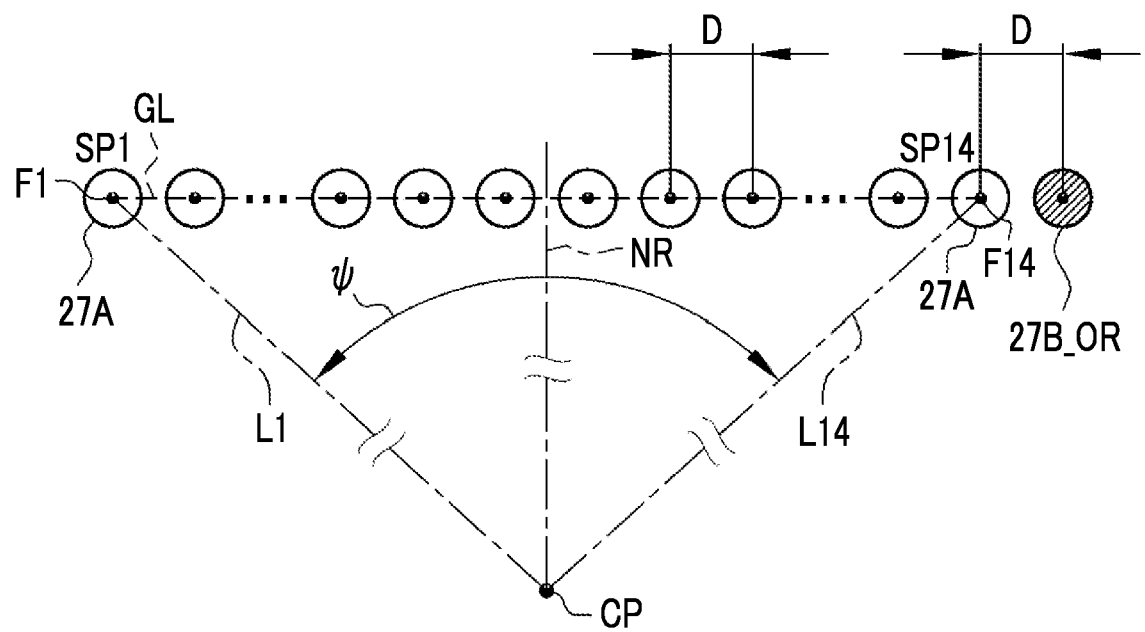
FIG. 14 is a diagram illustrating a second radiation tube that is disposed at a position outside a maximum scanning angle of the tomosynthesis imaging.

In a third embodiment illustrated in FIG. 14, a second radiation tube 27B_OR is disposed at a position outside the maximum scanning angle ψ.

In FIG. 14, the second radiation tube 27B_OR is disposed at a position outside the maximum scanning angle of tomosynthesis imaging which is defined by positions SP1 and S14 at both ends among a plurality of positions SP1 to SP14. In addition, the second radiation tube 27B_OR is disposed at a position that is outside the maximum scanning angle ψ and is at a distance (an interval D in FIG. 14) equal to or less than the interval D between the focuses F1 to F14 from one (the position SP14 in FIG. 14) of the positions SP1 and SP14.

As such, in the third embodiment, the second radiation tube 27B_OR is disposed at a position outside the maximum scanning angle ψ. Therefore, there is no possibility that the regularity of the intervals D between the focuses F1 to F14 will be disturbed and no concern that the process related to the generation of the tomographic image T will be complicated due to the presence of the second radiation tube 27B_OR. In addition, in the third embodiment, the second radiation tube 27B_OR is disposed at the position that is at a distance equal to or less than the interval D from one of the positions SP1 and SP14 at both ends. Therefore, the projection image output from the radiation detector 26 in the pre-imaging has been obtained by emitting the radiation 37 from substantially the same position as that in the tomosynthesis imaging. Therefore, it is possible to set the irradiation conditions more suitable for the tomosynthesis imaging than that in a case in which the second radiation tube 27B_OR is disposed at a position that is at a distance greater than the interval D.

Fourth Embodiment

Figure 15:
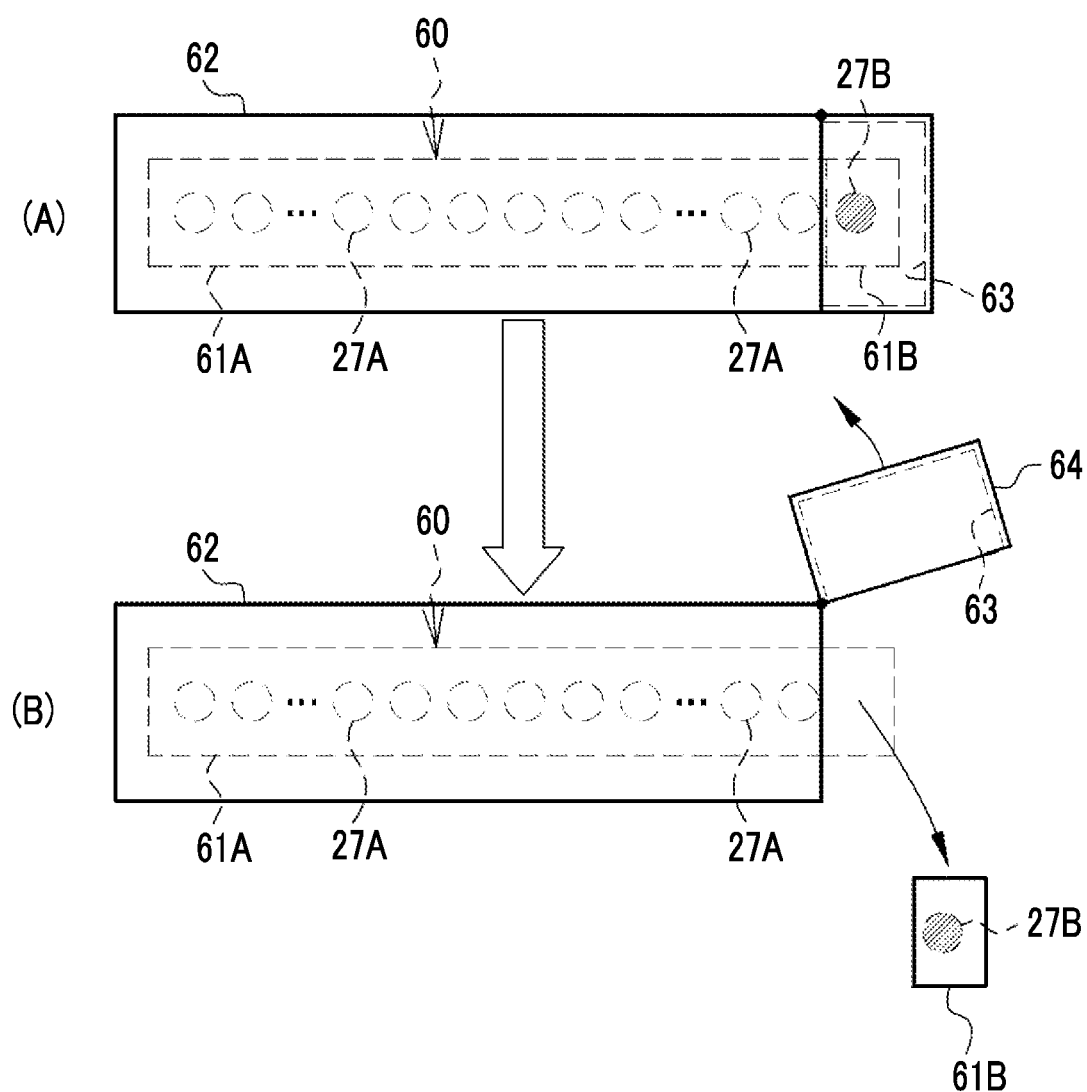
FIG. 15 is a diagram illustrating a fourth embodiment in which a second radiation tube is replaceable. (A) of FIG. 15 illustrates a state in which a cover of a radiation source accommodation portion is at a closed position, and (B) of FIG. 15 illustrates a state in which the cover is moved to an open position and a second housing accommodating a second radiation tube is removed.
Figure 16:
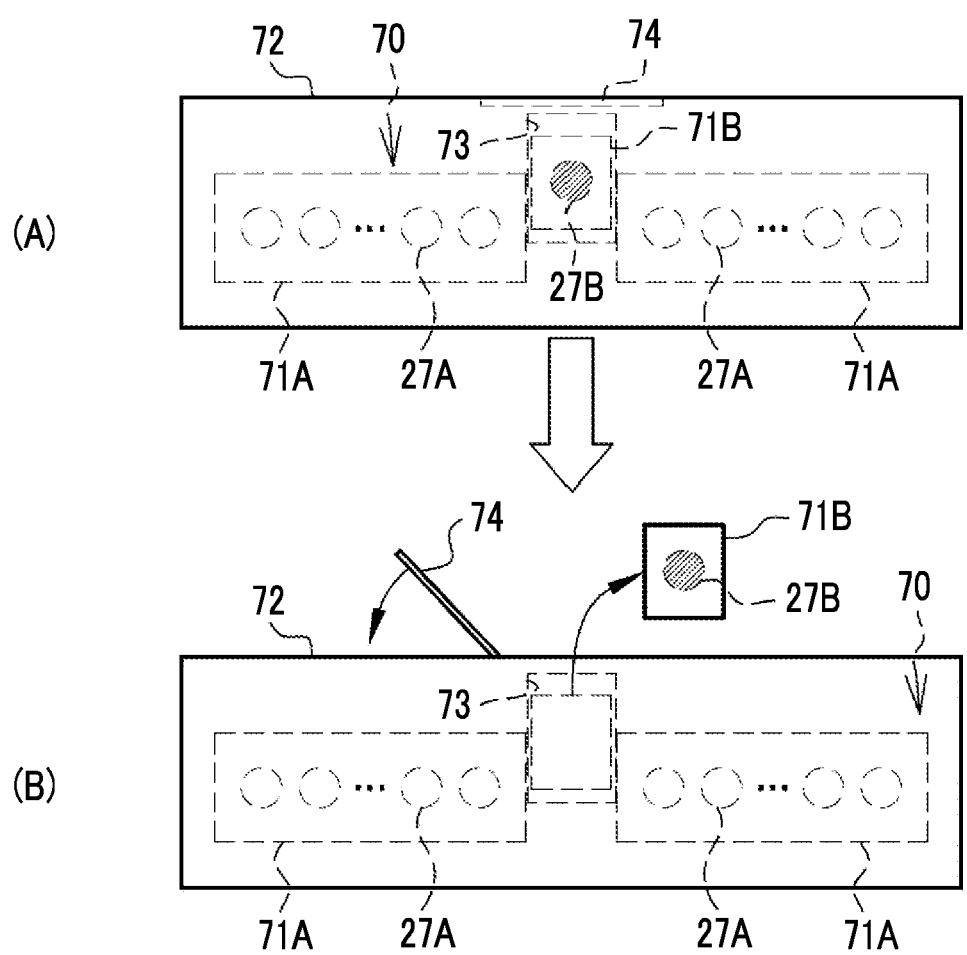
FIG. 16 is a diagram illustrating another example of the fourth embodiment in which a second radiation tube is replaceable. (A) of FIG. 16 illustrates a state in which a cover of a radiation source accommodation portion is at a closed position, and (B) of FIG. 16 illustrates a state in which the cover is moved to an open position and a second housing accommodating a second radiation tube is removed.

In a fourth embodiment illustrated in FIGS. 15 and 16, a second radiation tube 27B can be replaced.

In FIG. 15, a radiation source 60 includes a plurality of first radiation tubes 27A, one second radiation tube 27B, a first housing 61A that accommodates the first radiation tube 27A, and a second housing 61B that accommodates the second radiation tube 27B. The second radiation tube 27B is, for example, the second radiation tube 27B_OR according to the third embodiment which is disposed outside the maximum scanning angle ψ.

The radiation source accommodation portion 62 of the radiation source 60 is provided with an accommodation space 63 that accommodates the second housing 61B (second radiation tube 27B) such that the second housing 61B can be replaced and an openable and closable cover 64 that covers the accommodation space 63.

(A) of FIG. 15 illustrates a state in which the cover 64 is at a closed position. The cover 64 is changed from the closed position illustrated in (A) of FIG. 15 to an upper open position where the accommodation space 63 is exposed as illustrated in (B) of FIG. 15. Then, the second radiation tube 27B can be removed and replaced together with the second housing 61B.

A radiation source 70 illustrated in FIG. 16 includes a plurality of first radiation tubes 27A, one second radiation tube 27B, a first housing 71A that accommodates the first radiation tubes 27A, and a second housing 71B that accommodates the second radiation tube 27B. The second radiation tube 27B is, for example, the second radiation tube 27B according to the first embodiment which is disposed at the position offset to the rear side.

The radiation source accommodation portion 72 of the radiation source 70 is provided with an accommodation space 73 that accommodates the second housing 71B (second radiation tube 27B) such that the second housing 71B can be replaced and an openable and closable cover 74 that covers the accommodation space 73.

(A) of FIG. 16 illustrates a state in which the cover 74 is at a closed position. The cover 74 is changed from the closed position illustrated in (A) of FIG. 16 to an upper open position where the accommodation space 73 is exposed as illustrated in (B) of FIG. 16. Then, the second radiation tube 27B can be removed and replaced together with the second housing 71B.

As such, in the fourth embodiment, the radiation source includes a first housing that accommodates the first radiation tubes 27A and a second housing that accommodates the second radiation tube 27B. The radiation source accommodation portion is provided with a space that accommodates the second housing and an openable and closable cover that covers the accommodation space such that the second housing, that is, the second radiation tube 27B can be replaced. Therefore, it is possible to easily replace the second radiation tube 27B and maintenance is improved.

Since the second radiation tube 27B is used only for the pre-imaging, the progress of the deterioration of the performance of the second radiation tube 27B is slower than that of the first radiation tube 27A for tomosynthesis imaging which emits a higher dose of the radiation 37 than the pre-imaging. Therefore, it is considered that, even though the first radiation tube 27A reaches the usage limit due to deterioration, the second radiation tube 27B has not reached the usage limit and is still usable in many cases. In a case in which the second radiation tube 27B is replaceable, it is possible to effectively use the second radiation tube 27B which can still be used.

Figure 17:
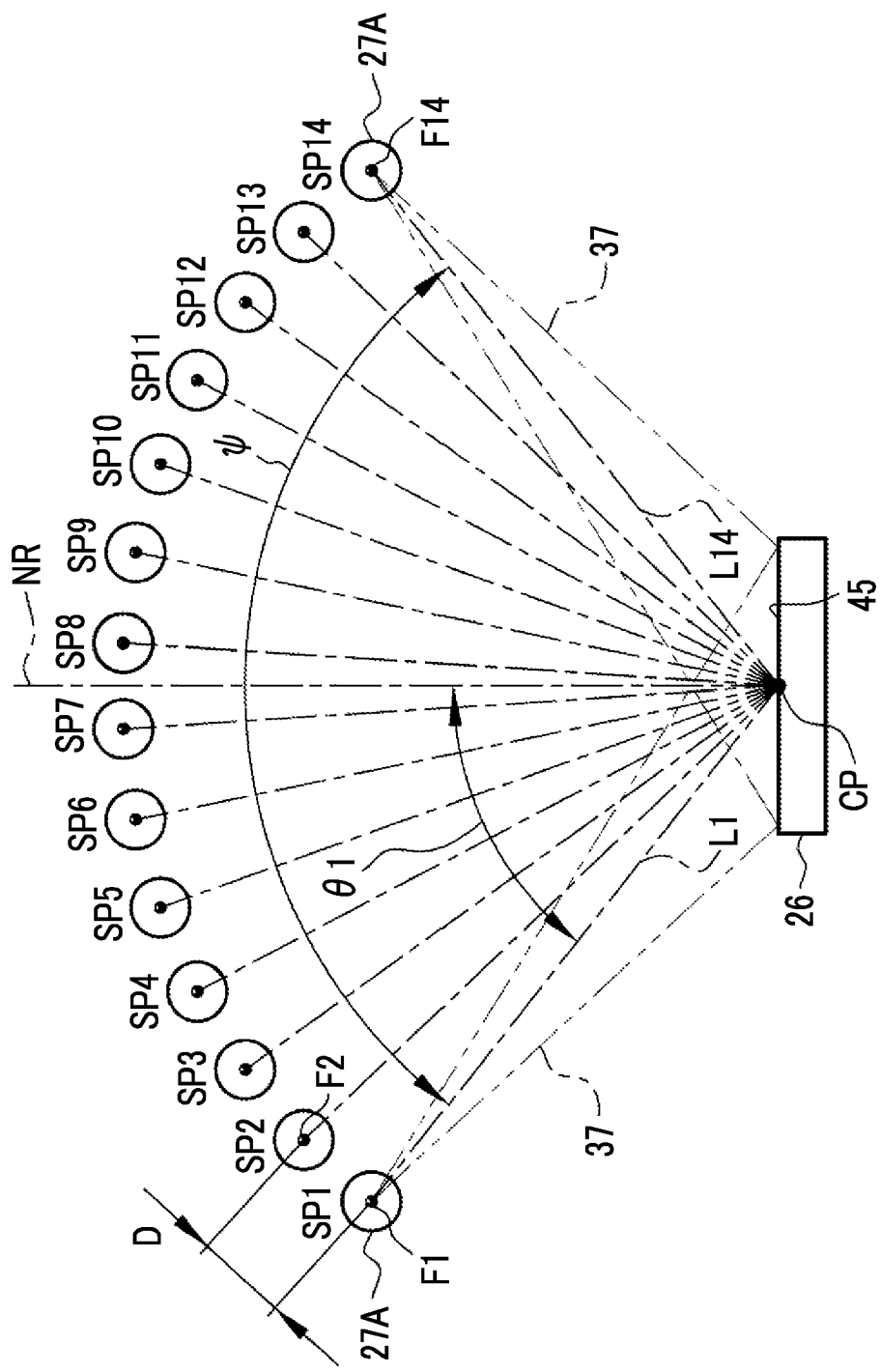
FIG. 17 is a diagram illustrating an example in which the first radiation tubes are disposed at a plurality of positions where the focuses of radiation are set so as to be arranged in an arc shape at equal intervals.

In each of the above-described embodiments, the positions where the first radiation tubes 27A are disposed are linearly arranged. However, the present disclosure is not limited thereto. As illustrated in FIG. 17, the plurality of positions SP1 to SP14 where the first radiation tubes 27A are disposed may be set so as to be arranged in an arc shape at equal intervals D. Even in a case in which the positions are arranged in the arc shape, the regularity of the arrangement positions SP1 to SP14 of the first radiation tubes 27A is ensured similarly to the case in which the positions are linearly arranged. Therefore, it is possible to simplify the process related to the generation of the tomographic image T.

Instead of the simple imaging in which the CC imaging illustrated in FIG. 5 and the MLO imaging illustrated in FIG. 6 are independently performed, a composite radiographic image equivalent to the radiographic image obtained by the simple imaging may be generated. The composite radiographic image is generated by performing a known composite image generation process, such as a minimum intensity projection method, for at least one of a plurality of projection images obtained by the tomosynthesis imaging and a plurality of tomographic images T generated by the tomographic image generation unit 52.

In each of the above-described embodiments, the mammography apparatus 10 is given as an example of the tomosynthesis imaging apparatus. In the related art, performing tomosynthesis imaging in the mammography apparatus 10 has been found to be useful as a method for easily finding lesions such as microcalcifications of the breast M. Therefore, it is preferable to apply the tomosynthesis imaging apparatus according to the present disclosure to the mammography apparatus 10.

Figure 18:
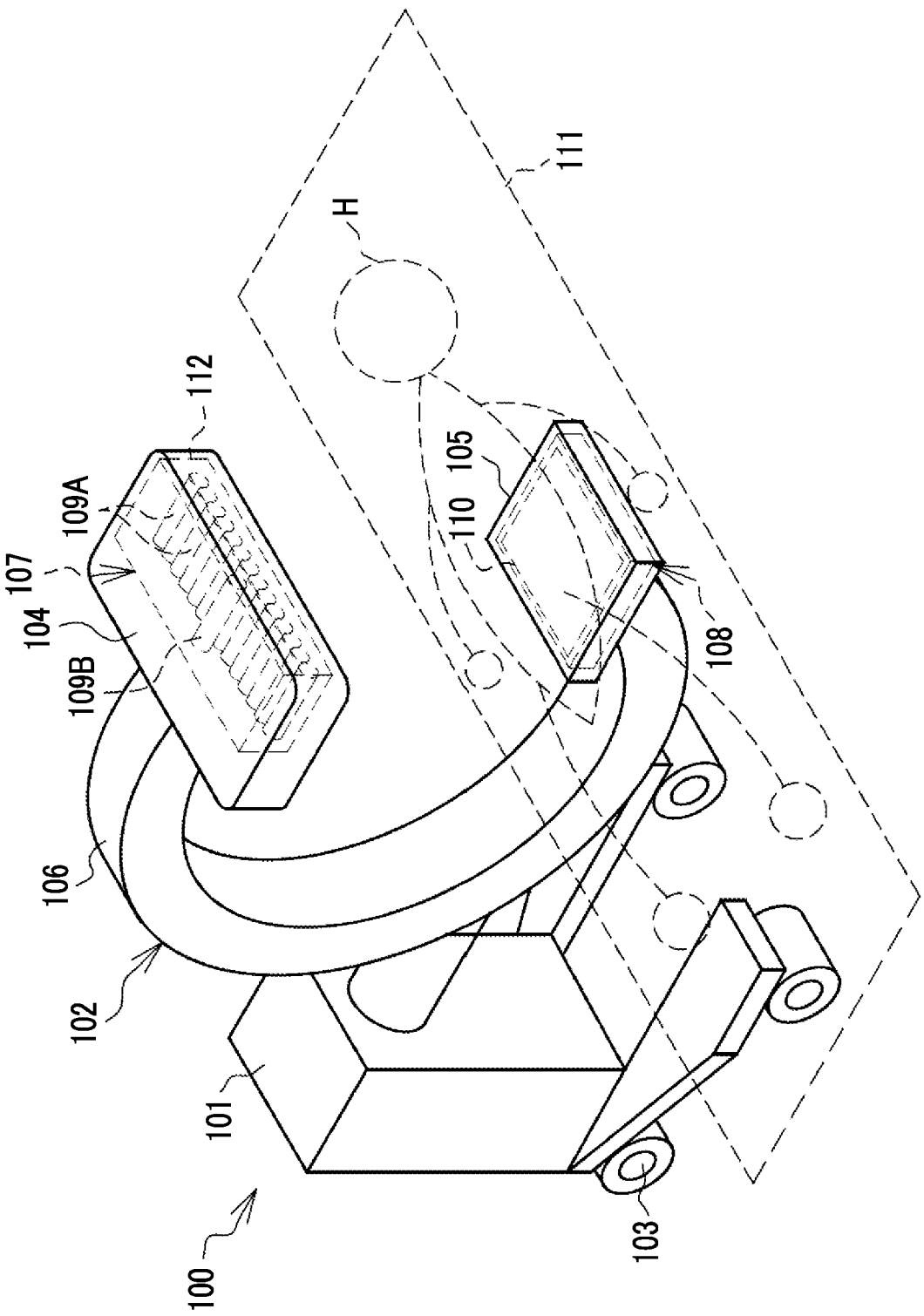
FIG. 18 is a diagram illustrating an imaging apparatus for surgery.

Of course, the tomosynthesis imaging apparatus according to the present disclosure may be applied to imaging apparatuses other than the mammography apparatus 10. For example, the tomosynthesis imaging apparatus according to the present disclosure may be applied to an imaging apparatus 100 illustrated in FIG. 18 which captures the image of the subject H during surgery.

The imaging apparatus 100 comprises an apparatus main body 101 having a control device (not illustrated) provided therein and an arm 102 having a substantially C-shape in a side view. A carriage 103 is attached to the apparatus main body 101 such that the apparatus main body 101 can be moved. The arm 102 includes a radiation source accommodation portion 104, a detector accommodation portion 105, and a main body portion 106. As in the mammography apparatus 10 illustrated in FIG. 1, the radiation source accommodation portion 104 accommodates a radiation source 107. In addition, the detector accommodation portion 105 accommodates a radiation detector 108. The radiation source accommodation portion 104 and the detector accommodation portion 105 are held by the main body portion 106 at a posture where they face each other.

The radiation source 107 and the radiation detector 108 have the same basic configurations as the radiation source 25 and the radiation detector 26 illustrated in FIG. 1, respectively. However, the imaging apparatus 100 captures an image of an object, such as the entire chest of the subject H, which is larger than the breast M. Therefore, a first radiation tube 109A and a second radiation tube 109B forming the radiation source 107 have a larger diameter than each of the radiation tubes 27A and 27B of the mammography apparatus 10. In addition, the radiation detector 108 has an imaging surface 110 whose area is larger than that of the imaging surface 45 of the radiation detector 26. The number of first radiation tubes 109A arranged may increase in order to respond to the capture of the image of a large object.

The detector accommodation portion 105 is inserted below a bed 111 on which the subject H lies supine. The bed 111 is made of a material that transmits the radiation 37. The radiation source accommodation portion 104 is provided above the subject H at a position that faces the detector accommodation portion 105 with the subject H interposed therebetween.

Similarly to the mammography apparatus 10, the imaging apparatus 100 performs pre-imaging using the second radiation tube 109B and performs tomosynthesis imaging using the first radiation tubes 109A. The imaging apparatus 100 can perform simple imaging using one first radiation tube 109A, in addition to the tomosynthesis imaging. In addition, instead of the simple imaging, the imaging apparatus 100 may generate a composite radiographic image. Further, the imaging apparatus 100 may capture both still radiographic images and moving radiographic images. Furthermore, reference numeral 112 indicates a housing for the radiation source 107.

The tomosynthesis imaging apparatus according to the present disclosure may be applied to a general radiography apparatus configured by combining a ceiling-suspended radiation source and an upright imaging table or a decubitus imaging table in which a radiation detector is set, in addition to the imaging apparatus 100 for surgery. Further, the tomosynthesis imaging apparatus according to the present disclosure may be applied to, for example, a cart-type mobile radiography apparatus which is moved to each hospital room and is used to capture the image of the subject H.

In each of the above-described embodiments, one second radiation tube is provided. However, a plurality of second radiation tubes may be provided.

In each of the above-described embodiments, each first radiation tube 27A has one focus F. However, the technology according to the present disclosure is not limited thereto. At least one of the plurality of first radiation tubes 27A may have a plurality of focuses F.

The following first to third configurations are described as the configuration in which one radiation tube has a plurality of focuses. In the first configuration, a plurality of cathodes are provided in one radiation tube and electrons collide with a plurality of different positions of an anode. In the second configuration, a plurality of areas for emitting the electron beams EB are provided in one field-emission-type cold cathode, such as the cathode 35, and electrons collide with a plurality of different positions of an anode. In the third configuration, the trajectory of electrons emitted from one cathode is changed such that electrons collide with a plurality of different positions of an anode. In the first and third configurations, the cathode may be a field-emission-type cold cathode, such as the cathode 35, or a hot cathode in which a filament is heated to emit thermal electrons.

Figure 19:
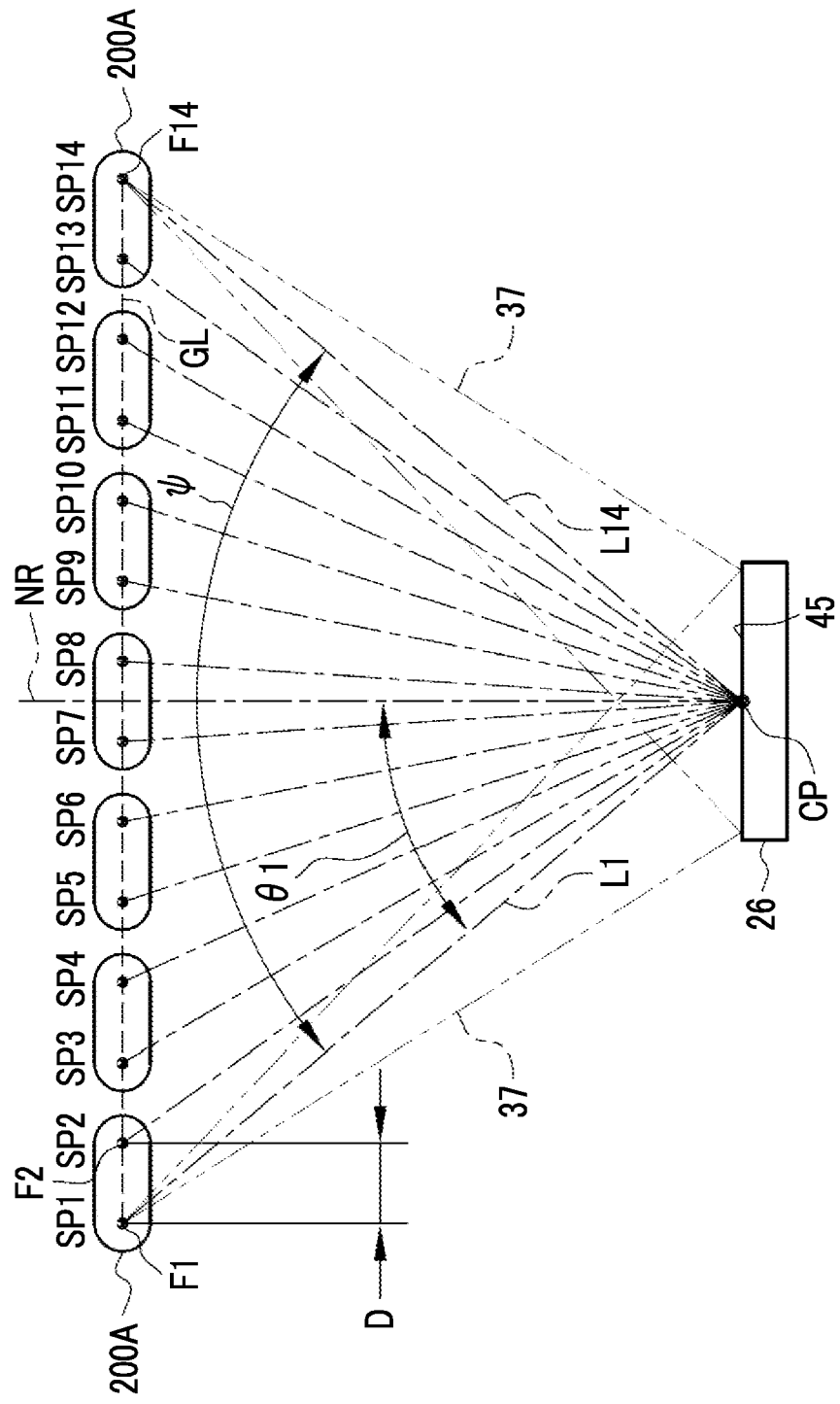
FIG. 19 is a diagram illustrating a configuration of a radiation tube having a plurality of focuses.

FIG. 19 illustrates a case in which first radiation tubes 200A each of which has two focuses F are used. That is, a radiation tube 200A having focuses F1 and F2, a radiation tube 200A having focuses F3 and F4, . . . , a radiation tube 200A having focuses F11 and F12, and a radiation tube 200A having focuses F13 and F14 are used.

As such, the first radiation tube may have a plurality of focuses F. In addition, the radiation source includes a first radiation tube having one focus F and a first radiation tube having a plurality of focuses F.

In the above-described embodiments, for example, the following various processors can be used as the hardware structure of processing units performing various processes, such as the control unit 50 (the pre-imaging control unit 50A and the tomosynthesis imaging control unit 50B), the irradiation condition setting unit 51, and the tomographic image generation unit 52. The various processors include a central processing unit (CPU) which is a general-purpose processor executing software to function as various processing units, a programmable logic device (PLD), such as a field programmable gate array (FPGA), which is a processor whose circuit configuration can be changed after manufacture, and a dedicated electric circuit, such as an application specific integrated circuit (ASIC), which is a processor having a dedicated circuit configuration designed to perform a specific process.

One processing unit may be configured by one of the various processors or a combination of two or more processors of the same type or different types (for example, a combination of a plurality of FPGAs or a combination of a CPU and an FPGA). In addition, a plurality of processing units may be configured by one processor.

A first example of the configuration in which a plurality of processing units are configured by one processor is an aspect in which one processor is configured by a combination of one or more CPUs and software and functions as a plurality of processing units. A representative example of this aspect is a client computer or a server computer. A second example of the configuration is an aspect in which a processor that implements the functions of the entire system including a plurality of processing units using one integrated circuit (IC) chip is used. A representative example of this aspect is a system-on-chip (SoC). As such, various processing units are configured by using one or more of the various processors as a hardware structure.

In addition, specifically, an electric circuit (circuitry) obtained by combining circuit elements, such as semiconductor elements, can be used as the hardware structure of the various processors.

In the technology according to the present disclosure, the above-mentioned various embodiments and various modification examples may be combined with each other. In addition, the present disclosure is not limited to the above-described embodiments and various configurations can be used without departing from the scope and spirit of the present disclosure.

What is claimed is:

1. A tomosynthesis imaging apparatus comprising:
a radiation detector that detects radiation transmitted through an object and has an imaging surface capturing a projection image of the object;
a radiation source including a plurality of first radiation tubes which are provided at a plurality of positions where the radiation is emitted to the imaging surface at different irradiation angles and a second radiation tube different from the first radiation tubes; and
a control unit that controls an operation of the radiation detector and the radiation source, the control unit being configured to perform tomosynthesis imaging, which captures a plurality of projection images of the object at different irradiation angles using the plurality of first radiation tubes, by adjusting at least one of a tube voltage, a tube current or an irradiation time of the tomosynthesis imaging, based on a result of pre-imaging using the second radiation tube.

2. The tomosynthesis imaging apparatus according to claim 1,
wherein focuses of the radiation at the plurality of positions are set so as to be arranged in a linear shape or an arc shape at equal intervals.

3. The tomosynthesis imaging apparatus according to claim 2,
wherein at least one of the plurality of first radiation tubes has one focus.

4. The tomosynthesis imaging apparatus according to claim 2,
wherein at least one of the plurality of first radiation tubes has a plurality of the focuses.

5. The tomosynthesis imaging apparatus according to claim 2,
wherein the second radiation tube is disposed at a position outside a maximum scanning angle of the tomosynthesis imaging which is defined by positions at both ends among the plurality of positions.

6. The tomosynthesis imaging apparatus according to claim 5,
wherein the second radiation tube is disposed at a position that is outside the maximum scanning angle and is at a distance equal to or less than the interval from one of the positions at both ends.

7. The tomosynthesis imaging apparatus according to claim 1,
wherein the second radiation tube is disposed at a position that is offset from the plurality of positions to a rear side which is a side opposite to an irradiation side of the radiation.

8. The tomosynthesis imaging apparatus according to claim 1,
wherein a diameter of the second radiation tube is less than a diameter of each of the plurality of first radiation tubes.

9. The tomosynthesis imaging apparatus according to claim 1,
wherein the second radiation tube is disposed at a position within a maximum scanning angle of the tomosynthesis imaging which is defined by positions at both ends among the plurality of positions.

10. The tomosynthesis imaging apparatus according to claim 9,
wherein the second radiation tube is disposed at a position corresponding to a center of the maximum scanning angle within the maximum scanning angle.

11. The tomosynthesis imaging apparatus according to claim 1,
wherein the radiation source includes a first housing that accommodates the first radiation tubes and a second housing that accommodates the second radiation tube, and
the second housing is replaceable.

12. The tomosynthesis imaging apparatus according to claim 11,
wherein a radiation source accommodation portion that accommodates the radiation source is provided with an accommodation space which accommodates the second housing such that the second housing is replaceable and an openable and closable cover which covers the accommodation space.

13. The tomosynthesis imaging apparatus according to claim 1,
wherein each of the first radiation tube and the second radiation tube includes a cathode that emits electrons and an anode with which the electrons collide and which emits the radiation.

14. The tomosynthesis imaging apparatus according to claim 13,
wherein the anode is a fixed anode.

15. The tomosynthesis imaging apparatus according to claim 13,
wherein the cathode is a field emission type including an electron emission source that emits an electron beam using a field emission phenomenon.

16. The tomosynthesis imaging apparatus according to claim 1,
wherein the tomosynthesis imaging apparatus is a mammography apparatus that uses a breast as the object.

17. The tomosynthesis imaging apparatus according to claim 1,
wherein the control unit is configured to perform the tomosynthesis imaging, which captures the plurality of projection images of the object at the different irradiation angles using the plurality of first radiation tubes, by adjusting at least one of the tube voltage, the tube current or the irradiation time of the tomosynthesis imaging, based on a density of an image obtained by the pre-imaging.

18. A method for operating a tomosynthesis imaging apparatus comprising a radiation detector that detects radiation transmitted through an object and has an imaging surface capturing a projection image of the object and a radiation source including a plurality of first radiation tubes which are provided at a plurality of positions where the radiation is emitted to the imaging surface at different irradiation angles and a second radiation tube different from the first radiation tubes, the method comprising:
  performing pre-imaging using the second radiation tube; and
  performing tomosynthesis imaging, which captures a plurality of projection images of the object at different irradiation angles using the plurality of first radiation tubes, by adjusting at least one of a tube voltage, a tube current or an irradiation time of the tomosynthesis imaging, based on a result of the pre-imaging.

19. A non-transitory computer-readable storage medium storing a program for operating a tomosynthesis imaging apparatus comprising a radiation detector that detects radiation transmitted through an object and has an imaging surface capturing a projection image of the object and a radiation source including a plurality of first radiation tubes which are provided at a plurality of positions where the radiation is emitted to the imaging surface at different irradiation angles and a second radiation tube different from the first radiation tubes, the program causing a computer to execute a process comprising:
  performing pre-imaging using the second radiation tube; and
  performing tomosynthesis imaging, which captures a plurality of projection images of the object at different irradiation angles using the plurality of first radiation tubes, by adjusting at least one of a tube voltage, a tube current or an irradiation time of the tomosynthesis imaging, based on a result of the pre-imaging.

* * * * *